(12) United States Patent
Song et al.

(10) Patent No.: US 12,167,911 B2
(45) Date of Patent: Dec. 17, 2024

(54) METHOD AND APPARATUS FOR MUSCLE TONE AND LIMB MOVEMENT MEASUREMENT AND ASSESSMENT

(71) Applicants: The Board of Trustees of the University of Illinois, Urbana, IL (US); OSF Healthcare System, Peoria, IL (US)

(72) Inventors: Seung Yun Song, Champaign, IL (US); Elizabeth T. Hsiao-Wecksler, Urbana, IL (US); Christopher M. Zallek, Peoria Heights, IL (US)

(73) Assignees: THE BOARD OF TRUSTEES OF THE UNIVERSITY OF ILLINOIS, Urbana, IL (US); OSF HEALTHCARE SYSTEM, Peoria, IL (US)

( * ) Notice: Subject to any disclaimer, the term of this patent is extended or adjusted under 35 U.S.C. 154(b) by 193 days.

(21) Appl. No.: 17/147,654

(22) Filed: Jan. 13, 2021

(65) Prior Publication Data

US 2021/0219872 A1 Jul. 22, 2021

Related U.S. Application Data

(60) Provisional application No. 62/962,571, filed on Jan. 17, 2020.

(51) Int. Cl.
*A61B 5/11* (2006.01)
*A61B 5/00* (2006.01)
*A61B 5/107* (2006.01)

(52) U.S. Cl.
CPC .......... *A61B 5/1114* (2013.01); *A61B 5/0004* (2013.01); *A61B 5/1072* (2013.01);
(Continued)

(58) Field of Classification Search
CPC ... A61B 5/1114; A61B 5/0004; A61B 5/1072; A61B 5/1075; A61B 5/1107;
(Continued)

(56) References Cited

U.S. PATENT DOCUMENTS 7,478,009 B2    1/2009   Cabrera et al.
8,467,979 B2 *   6/2013   Sobolewski ......... A43B 7/1445
                                                         600/595

(Continued)

FOREIGN PATENT DOCUMENTS

WO    WO15135981 A1    9/2015

OTHER PUBLICATIONS

"Sanger T, et al. Classification and Definition of Disorders Causing Hypertonia in Childhood. Jan. 1, 2003. American Academy of Pediatrics. vol. 111, Issue 1. p. 89" (Year: 2003).*

(Continued)

*Primary Examiner* — Benjamin S Melhus
*Assistant Examiner* — Severo Antonio P Lopez
(74) *Attorney, Agent, or Firm* — Crowell & Moring LLP

(57) ABSTRACT

The disclosure is directed to a method and apparatus for measuring and assessing limb movement properties. The method includes conducting a test protocol with a position, velocity, and resistance meter (PVRM); and obtaining raw data from the PVRM and transmitting the raw data from the PVRM to an electronic device. The method includes processing the raw data to obtain processed data; and obtaining a set of parameters based on the processed data. The method includes obtaining a classification result according to a classifying algorithm based on the set of parameters; and assessing, recording, and displaying a limb movement property according to the classification result.

19 Claims, 19 Drawing Sheets

(52) U.S. Cl.
CPC .......... *A61B 5/1075* (2013.01); *A61B 5/1107* (2013.01); *A61B 5/1121* (2013.01); *A61B 5/7267* (2013.01); *A61B 2562/0219* (2013.01); *A61B 2562/0252* (2013.01)

(58) Field of Classification Search
CPC ................ A61B 5/1121; A61B 5/7267; A61B 2562/0219; A61B 2562/0252
See application file for complete search history.

(56) References Cited

U.S. PATENT DOCUMENTS

| | | | |
|---|---|---|---|
| 9,265,451 | B2 | 2/2016 | Levin et al. |
| 2007/0027631 | A1* | 2/2007 | Cabrera ............... A61B 5/1124 702/19 |
| 2013/0303947 | A1 | 11/2013 | Gamet et al. |
| 2014/0074179 | A1 | 3/2014 | Heldman et al. |
| 2014/0277542 | A1* | 9/2014 | Stein ..................... A61F 2/4657 623/20.32 |
| 2016/0317066 | A1 | 11/2016 | Wang et al. |

OTHER PUBLICATIONS

"Park J, et al. Artificial Neural Network Learns Clinical Assessment of Spasticity in Modified Ashworth Scale. Oct. 2019. Archives of Physical Medicine and Rehabilitation. vol. 100, Issue 10. p. 1908" (Year: 2019).*
"Pandyan A. Biomechanical examination of a commonly used measure of spasticity. Clinical Biomechanics. Dec. 2001. vol. 16, Issue 10. p. 861" (Year: 2001).*
"Song S, et al. Design of a Portable Position, Velocity, and Resistance Meter (PVRM) for Convenient Clinical Evaluation of Spasticity or Rigidity. Apr. 10, 2017. p. 1" (Year: 2017).*
"Cano-de-la-Cuerda R. Isokinetic dynamometry as a technologic assessment tool for trunk rigidity in Parkinson's disease patients. 2014. NeuroRehabilitation. vol. 35. p. 494" (Year: 2014).*
"Multiple Scerlosis FAQs" [Online]. Available: htlps://www.nationalmssociety.org/What-is-MS/MS-FAQ-s#question-What-are-the-typical-symptoms-of-MS. [Accessed: Aug. 1, 2019].
Allison et al., "Reliability of the Modified Ashworth Scale in the assessment of plantarflexor muscle spasticity in patients with traumatic brain injury," *International Journal of Rehabilitation Research*, vol. 19. ( 1996) pp. 67-68.
Blackburn et al., "Reliability of Measurements Obtained With the Modified Ashworth Scale in the Lower Extremities of People With Stroke," *Physical Therapy*, 67:2 (1987) pp. 206-207.
Bohannon et al. "Interrater Reliability of a Modified Ashworth Scale of Muscle Spasticity," *Physical Therapy*, 67:2 (1987) pp. 206-207.
Caslake et al., "Parkinson's disease misdiagnosed as stroke," *BMJ Case Reports*, (2009) pp. 1-3.
Chittenden Symposium on Assistive Technologies in Health, iHotel (PowerPoint presented only the hardware) pp. 1-3.
Craig "Introduction to Robotics," *Pearson Education, Inc.*, (2005) pp. 1-408.
Craven et al., "Modified Ashworth scale reliability for measurement of lower extremity spasticity among patients with SCI," *Spinal Cord* 48 (2010) pp. 207-213.
de Leva, "Adjustments to Zatsiorsky-Seluyanov's Segment Inertia Parameters," *J. Biomechanics*, 29:9 (1996) pp. 1223-1230.
Diebel, Representing Attitude: Euler Angles, Unit Quaternions, and Rotation Vectors, Matrix, vol. 58 (2006) pp. 1-35.
Geminiani et al., "Interobserver Reliability Between Neurologists in Training of Parkinson's Disease Rating Scales A Multicenter Study," *Movement Disorders*, 6:4 (1991) pp. 330-335.
Ginanneschi et al., "Evaluation of Parkinson's Disease: Reliability of Three Rating Scales," *Neuroepidemiology*, vol. 7 (1988) pp. 38-41.

Goetz et al., "Movement Disorder Society-Sponsored Revision of the Unified Parkinson's Disease Rating Scale (MDS-UPDRS): Process, Format, and Clinimetric Testing Plan," *Movement Disorders* 22:1 (2007) pp. 41-47.
Jankovic, "Parkinson's disease: clinical features and diagnosis," *J. Neurol Neurosurg Psychiatry*, vol. 79 ((2008) pp. 368-376.
Kobayashi et al., "Quantitative measurement of spastic ankle joint stiffness using a manual device: A preliminary study," *Journal of Biomechanics*, vol. 43 (2010) pp. 1831-1834.
Kuipers, "Quaternions and Rotation Sequences," *Coral Press* (2000) pp. 127-143.
Lee et al., "Estimation of Attitude and External Acceleration Using Inertial Sensor Measurement During Various Dynamic Conditions," *IEEE Transactions On Instrumentation And Measurement*, 61:8, (2012) pp. 2262-2273.
Lee et al., "Quantitative analysis of the velocity related pathophysiology of spasticity and rigidity in the elbow flexors," *J. Neurol Neurosurg Psychiatry*; vol. 72 (2002) pp. 621-629.
Lorentzen et al., "Assessment of a portable device for the quantitative measurement of ankle joint stiffness in spastic individuals," *Clinical Neurophysiology*, vol. 123 (2012) pp. 1371-1382.
Mason "Mechanics of Robotic Manipulation," *MIT Press* (2001) pp. 1-278.
Mutlu et al., "Reliability of Ashworth and Modified Ashworth Scales in Children with Spastic Cerebral Palsy," *BMC Musculoskeletal Disorders*, 9:44 (2008) pp. 1-8.
Pandyan et al., "Biomechanical examination of a commonly used measure of spasticity," *Clinical Biomechanics*, vol. 16 (2001) pp. 859-865.
Patrick et al., "Quantification of the UPDRS Rigidity Scale," *IEEE Transactions On Neural Systems And Rehabilitation Engineering*, 9:1 (2001) pp. 31-41.
Song et al., "Quantification of Spasticity and Rigidity for Biceps and Triceps Using the PVRM (Position, Velocity, and Resistance Meter)", *M.S. Thesis, Department of Mechanical Science and Engineering, University of Illinois at Urbana-Champaign*, (2019) pp. 1-118.
Song et al., "Design and Validation of a Measurement Device (The PVRM—Position, Velocity, and Force Meter) for Quantifying Spasticity and Rigidity," *IEEE Transactions on Biomedical Engineering, in prep.* pp. 1-9.
Song et al., Design of a Portable Position, Velocity, and Resistance Meter (PVRM) for Convenient Clinical Evaluation of Spasticity or Rigidity, *Proceedings of the 2017 Design of Medical Devices Conference* (2017) pp. 1-2.
Song et al., "Measuring Relative Joint Angles Using Inertial Measurement Units without Magnetometers," *IEEE Sensors Journal*, pp. 1-8.
Song et al., "Validation of wearable Position, Velocity and Resistance Meter for Assessing Spasticity and Rigidity," *Proceedings of the 2018 Design of Medical Devices Conference* (2018) pp. 1-3.
Song et al., Quantification of Spasticity in Upper-arm Muscle Using the PVRM, pp. 1-16.
Song et al., Quantification of Upper-arm Spasticity and Rigidity using the Position, Velocity, and Resistance Meter, *Clinical Neurophysiology, in prep*, pp. 1-36.
Van Dillen et al., "Interrater Reliability of a Clinical Scale of Rigidity," *Phys. Ther.*, 68:11, (1988) pp. 1679-1681.
Vanhoutte et al., "Modifying the Medical Research Council Grading System through Rasch Analyses," *Brain*, 135:(Pt 5), (2012) pp. 1639-1649.
Yam et al., "Interrater Reliability of Modified Ashworth Scale and Modified Tardieu Scale in Children with Spastic Cerebral Palsy," *J. Child Neurol.*, 21:12 (2006) pp. 1031-1035.
Yun et al., Design, Implementation, and Experimental Results of a Quaternion-Based Kalman Filter for Human Body Motion Tracking, *IEEE Transactions On Robotics*, 22:6 (2006) pp. 1-12.
Yun et al., *A Simplified Quaternion-Based Algorithm for Orientation Estimation from Earth Gravity and Magnetic Field Measurements, IEEE Transactions On Instrumentation And Measurement*, 57:3, (2008) pp. 638-650

* cited by examiner

200 collecting raw data by a PVRM;
210 processing raw data to obtain processed data;
220 processing the processed data to obtain a set of parameters
230 obtaining a classification result based on the set of the parameters according to a classification algorithm
240

Figure 2

600 conducting a test protocol with a position, velocity, and resistance meter (PVRM); 610 obtaining raw data from the PVRM and transmitting the raw data from the PVRM to an electronic device; 620 processing the raw data to obtain processed data 630 obtaining a set of parameters based on the processed data; 640 obtaining a classification result according to a classifying algorithm based on the set of parameter; and assessing a limb movement property according to the classification result 650 displaying and recording the set of parameters. 660

Figure 6A

METHOD AND APPARATUS FOR MUSCLE TONE AND LIMB MOVEMENT MEASUREMENT AND ASSESSMENT

RELATED APPLICATION

This application claims priority to Provisional Application No. 62/962,571 filed on Jan. 17, 2020, which is incorporated by reference in its entirety.

BACKGROUND

1. Technical Field

The present disclosure relates to a method and apparatus for assessing limb movement properties affected by muscle tone and other neurologic or orthopedic conditions. In particular, the present disclosure relates to a method and apparatus for evaluating muscle tone, muscle strength, limb movements, and identifying abnormalities of tone, strength, and limb movement.

2. Background Information

In a clinical setting, joint movement, muscle tone, and strength may need assessment. There are a few conventional standard scales that a clinician uses to grade muscle tone. One conventional assessment to grade spasticity of muscle tone is the Modified Ashworth Scale (MAS). One conventional assessment to grade rigidity of muscle tone is the motor section of Unified Parkinson's Disease Rating Scale (UPDRS). Both scales need a clinician to manually move the patient's affected limb while intuitively monitoring for increased muscle stiffness, leading to high variability in measurements, low reliability and low accuracy of the assessment. One conventional assessment to grade muscle strength is the Medical Research Council (MRC) for Muscle Strength. The test is dependent on examiner technique and also patient effort, which may be poor in some patients, owing to pain, proper comprehension of instructions, or psychological causes. The grading system of MRC classifies strength level but does not quantify strength.

The present disclosure is directed toward addressing one or more drawbacks, including but not limited to those set forth above. The present disclosure may reduce variability in measurements, and may improve accuracy of evaluating muscle tone and joint movement.

SUMMARY

The present disclosure describes a method for measuring and assessing limb movement properties. The method includes conducting a test protocol with a Position, Velocity, and Resistance Meter (PVRM); and obtaining raw data from the PVRM and transmitting the raw data from the PVRM to an electronic device. The method includes processing the raw data to obtain processed data; and obtaining a set of parameters based on the processed data. The method includes obtaining a classification result according to a classifying algorithm based on the set of parameters; and assessing limb movement properties according to the classification result.

The present disclosure describes an apparatus for measuring and assessing limb movement properties. The apparatus includes a Position, Velocity, and Resistance Meter (PVRM); and an electronic device in communication with the PVRM. The electronic device includes a memory for storing instructions, and a processor in communication with the memory. When the processor executes the instructions, the processor is configured to cause the apparatus to conduct a test protocol with the PVRM, obtain raw data from the PVRM, and transmit the raw data from the PVRM to the electronic device. When the processor executes the instructions, the processor is configured to cause the apparatus to process the raw data to obtain processed data, and obtain a set of parameters based on the processed data. When the processor executes the instructions, the processor is configured to cause the apparatus to obtain a classification result according to a classifying algorithm based on the set of parameters, and assess a limb movement properties according to the classification result.

BRIEF DESCRIPTION OF THE DRAWINGS

The system, device, product, and/or method described below may be better understood with reference to the following drawings and description of non-limiting and non-exhaustive embodiments. The components in the drawings are not necessarily to scale. Emphasis instead is placed upon illustrating the principles of the disclosure.

FIG. 2 describes a flow chart of a method from collecting raw data to classification using set of parameters.

FIG. 6A describes a flow chart describing the overview of the use of PVRM, processing and analysis of data.

Figure 1:
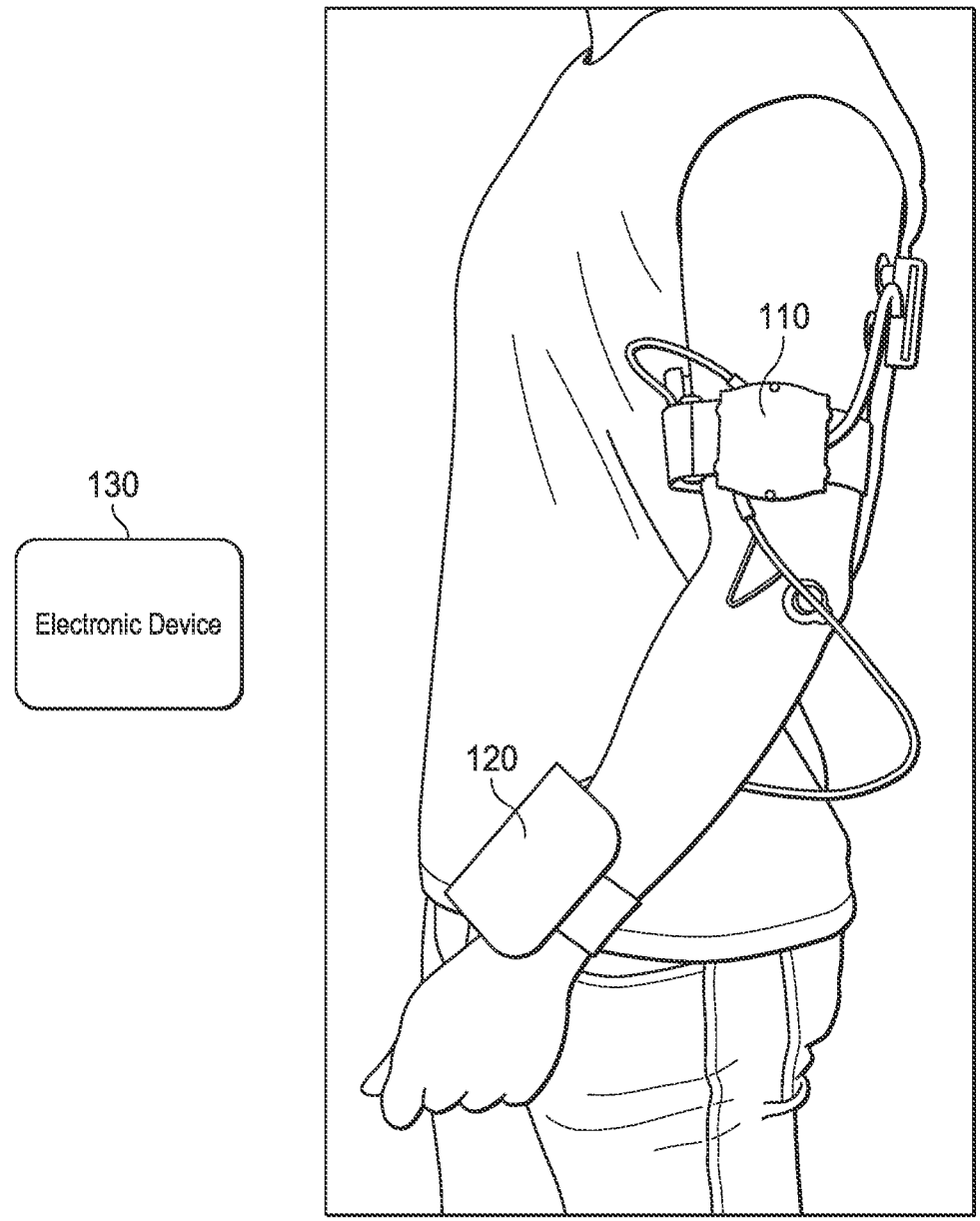
FIG. 1 describes the electronic device and the PVRM modules attached on a human subject.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION OF THE DISCLOSURE

The disclosed systems and methods will now be described in detail hereinafter with reference to the accompanied drawings, which form a part of the present application, and which show, by way of illustration, specific examples of embodiments. Please note that the systems and methods may, however, be embodied in a variety of different forms and, therefore, the covered or claimed subject matter is intended to be construed as not being limited to any of the embodiments to be set forth below. Please also note that the disclosure may be embodied as methods, devices, components, or systems. Accordingly, embodiments of the disclosed system and methods may, for example, take the form of hardware, software, firmware or any combination thereof.

Throughout the specification and claims, terms may have nuanced meanings suggested or implied in context beyond an explicitly stated meaning. Likewise, the phrase "in one embodiment" or "in some embodiments" as used herein does not necessarily refer to the same embodiment and the phrase "in another embodiment" or "in other embodiments" as used herein does not necessarily refer to a different embodiment. It is intended, for example, that claimed subject matter may include combinations of exemplary embodiments in whole or in part. Moreover, the phrase "in one implementation", "in another implementation", or "in some implementations" as used herein does not necessarily refer to the same implementation or different implementation. It is intended, for example, that claimed subject matter may include combinations of the disclosed features from the implementations in whole or in part.

In general, terminology may be understood at least in part from usage in context. For example, terms, such as "and", "or", or "and/or," as used herein may include a variety of meanings that may depend at least in part upon the context in which such terms are used. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

The present disclosure describes embodiments of methods and apparatus for accurately evaluating muscle tone and joint movement.

In one embodiment, referring to FIG. 1, an apparatus may include a main module 110 and a moving module 120. The main module and/or the moving module may include one or more sensors to measure a position, velocity, and/or resistance, which may refer as a Position, Velocity, and Resistance Meter (PVRM). A main module 110 may be referred to as a primary module; and a moving module 120 may be referred to as a secondary module. The main module 110 may be placed at a midpoint of a stationary body segment (e.g., upper arm, thigh), and the moving module 120 may be placed on a moving body segment (e.g., a forearm near the wrist, leg near the ankle). The PVRM may be use for any large articulating joint (shoulder, elbow, wrist, hip, knee, ankle, and possibly torso). During the movement of the moving body segment relative to the stationary body segment, the main module may generate a first set of raw data, and the moving module may generate a second set of raw data. The first and second sets of raw data may be transmitted from the main and moving modules to an electronic device 130. The electronic device 130 may process the received raw data to obtain processed data. Optionally, the electronic device 130 may display and/or record the processed data. The electronic device 130 may, according to a classification algorithm, obtain a classification result quantifying a severity of spasticity and/or rigidity.

In one embodiment, referring to FIG. 2, a method 200 may include step 210: collecting raw data by a PVRM; step 220, processing raw data to obtain processed data; step 230, processing the processed data to obtain a set of parameters; and step 240, obtaining a classification result based on the set of the parameters according to a classification algorithm. In one implementation, the processed data may include joint angular position ($\theta$), velocity ($\dot{\theta}$), acceleration ($\ddot{\theta}$), and muscle resistance ($\tau$) during a clinical assessment. In another implementation, the set of parameters may include one or more of the following variables: range of motion ($\theta_{ROM}$), peak muscle resistance ($\tau_{pk}$), change in peak muscle resistance at different speeds ($\Delta\tau_{pk}$), average muscle resistance ($\tau_{avg}$), catch angle ($\theta_{catch}$), max stretch speed ($\omega_{max}$), and local max stretch speed ($\omega_{local,max}$). The classification algorithm may identify a type and/or a degree of abnormal muscle or joint behavior based on the set of parameters, so that the method may identify types and degree of unhealthy conditions such as spasticity, rigidity, and weakness in strength.

Optionally, the method 200 may include displaying and/or storing one or more of the following: the raw data, the processed data, the set of parameters, and the classification result.

Optionally, the method 200 may include analyzing the stored data to reconstruct a history of a patient's limb movement properties, so as to monitor the progression of the disorder and tailor the treatment plans.

The present disclosure may benefit different patient populations such as patients with neurological disorders, or patients who underwent orthopedic surgery/injury.

Traditional clinical assessments of muscle tone/joint movement for patients with neurological disorders and for patients with orthopedic problems may be inaccurate and unreliable due to heavy reliance on clinician's subjective interpretation of qualitative scales.

In the case of patients with neurological disorders affecting muscle tone (resistance to passive manipulation), referring to Table 1, a traditional scale for assessing spasticity is the Modified Ashworth Scale (MAS), which may be applied to patients/subjects with upper motor neuron damage such as cerebral palsy, stroke, and multiple sclerosis. Referring to Table 2, a traditional scale for assessing rigidity is the motor section of Unified Parkinson's Disease Rating Scale (UPDRS), which may be applied to patients with Parkinson's disease and/or other Parkinson syndromes. Both scales require a clinician to manually move the patient's affected limb while intuitively monitoring for increased muscle stiffness.

Figure 3A:
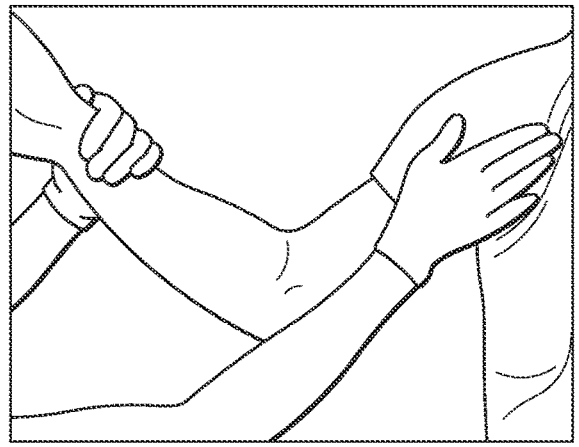
FIG. 3A describes an example wherein a clinician manually moves a patient's affect limb.
Figure 3B:
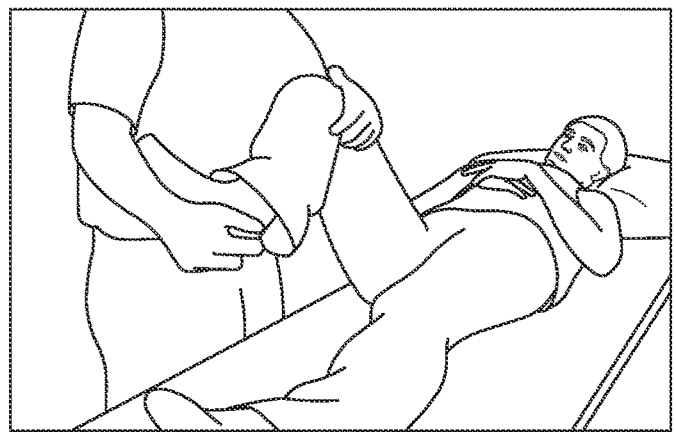
FIG. 3B describes an example wherein a clinician manually moves a patient's affect limb.
Figure 3C:
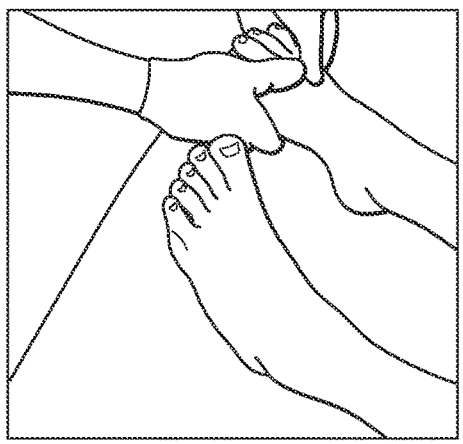
FIG. 3C describes an example wherein a clinician manually moves a patient's affect limb.

FIGS. 3A-3C show some examples wherein a clinician manually moves a patient's affect limb using conventional diagnostic methods. Relying mostly on past training and experience, the clinician may determine a severity level of muscle tone into different levels that are qualitatively described in the widely accepted clinical scales. The qualitative descriptions of different levels of rigidity and/or spasticity introduce subjective interpretation of the scale, causing inconsistent ratings and difficulty for teaching proper assessment techniques. For example, with conventional methods, clinicians may have different interpretations of the descriptive words such as "slight increase" or "minimal resistance."

TABLE 1

Modified Ashworth Scale (MAS) for spasticity assessment

| MAS Score | Qualitative Description |
|---|---|
| 0 | No increase in muscle tone |
| 1 | Slight increase in tone giving "a catch" when the body segment is moved in flexion or extension |
| 2 | A catch then minimal resistance through less than half the range of movement |
| 3 | Marked increase in tone with a catch followed by resistance through more than half the range of motion, but the body segment is still easily moved |
| 4 | Considerable increase in tone and passive movement is difficult |
| 5 | The body segment is rigid in flexion or extension |

TABLE 2

Unified Parkinson's Disease Rating Scale (UPDRS) rigidity motor section

| UPDRS Score | Qualitative Description |
|---|---|
| 0 | No rigidity |
| 1 | Rigidity only detected with activation maneuver |
| 2 | Rigidity detected w/o the activation maneuver, but full range of motion is easily achieved. |
| 3 | Rigidity detected w/o the activation maneuver; full range of motion is achieved w/effort. |
| 4 | Rigidity detected without the activation maneuver and full range of motion not achieved. |

When patients have weakness symptoms, referring to Table 3, a conventional clinical assessment used may be the Medical Research Council (MRC) for Muscle Strength. The clinician may ask the patient to exert isometric contraction of the muscle of interest while the clinician provides the resistance. There is some variability between examiners for the maximal resistance that they may apply, as some examiners may be stronger than other examiners. A performed test does not account for musculoskeletal conditions that may make testing painful or difficult to tolerate, such as tendinopathy or arthritis. The test may be dependent on patient effort, which may be poor in some patients, owing to pain, proper comprehension of instructions, or psychological causes. The grading system classifies strength level but does not directly quantify strength. The present disclosure may aid the assessment of muscle strength with more accuracy and resolution since the present disclosure utilizes quantitative biomechanical data.

TABLE 3

Medical Research Council Manual Muscle Testing scale

| MRC Score | Qualitative Description |
|---|---|
| 0 | No muscle activation |
| 1 | Trace muscle activation, such as a twitch, without achieving full range of motion |
| 2 | Muscle activation with gravity eliminated, achieving full range of motion |
| 3 | Muscle activation against gravity, full range of motion |
| 4 | Muscle activation against some resistance, full range of motion |
| 5 | Muscle activation against examiner's full resistance, full range of motion |

There may be three problems associated with the conventional clinical assessment scales: 1) the subjective nature of this method introduces inconsistent evaluation, 2) the qualitative scale imposes difficulty for inexperienced clinicians to properly learn this practice, and 3) lack of quantitative data of muscle stiffness poses difficulty to assess the efficacy of treatments. Regardless of the branch of medicine, experienced clinicians may be needed for accurate assessment since they may detect the complex and overlapping motor symptoms displayed by patients. In addition, these symptoms vary greatly among patients and across time of day. There may be no conventional accurate and consistent quantified tests for these symptoms. It may be not uncommon for experienced clinicians to misdiagnose the physical findings. For example, spasticity may be misdiagnosed as rigidity. This misdiagnosis may lead to significant delay in referral to specialist care and consideration of appropriate therapy. The present disclosure describes methods and devices for accurately assessing the muscle condition to facilitate providing appropriate care for patients with symptoms of neurological disorders.

The present disclosure describes an embodiment of PVRM, which is configured to measure kinematic and kinetic data that may be used to objectively measure joint movement and muscle tone. The PVRM may provide more accurate joint data and alleviate the clinician's heavy reliance on their experience and subjective interpretation of the clinical scales. Inexperienced clinicians may assess muscle tone and joint movement with the aid of the PVRM. For patients with neurological disorders, this present disclosure may help the screening process for patients with these disorders at an early stage (e.g. during a health check-up from a general practitioner) by detecting and classifying the type of abnormal muscle behavior and leading them to receive proper treatment plans.

The present disclosure may bring benefits to different groups: patients, clinicians, medical researchers, pharmaceutical companies, and health insurance companies. By being able to accurately assess the muscle and joint behavior, patients and clinicians may tailor the treatment plans (e.g., adjusting dosages of medication). Also, the present disclosure may provide insurance companies with more objective and quantitative data to justify the coverage for treating abnormal muscle or limb movement properties. Medical researchers or pharmaceutical companies may quantify the efficacy of newly developed therapy or surgery treating musculoskeletal disorders. For example, quantifying the increase in mobility and strength after a novel knee replacement surgery may be done by using the present disclosure. This present disclosure may accelerate the R&D process of treatment methods (e.g., medical devices, drugs, surgeries) for muscle conditions while decreasing cost and time. For example, pharmaceutical companies developing a new drug for treating spasticity may quantify the efficacy of their new drug using the PVRM to measure the level of spasticity before and after taking their drug. The database generated from the present disclosure may potentially be utilized to create a new rigidity and spasticity assessment scales that are more comprehensive, inclusive, and objective than the conventional subjective MAS and UPDRS scales. Like the use of thermometers and sphygmomanometers to record body temperature and blood pressure, the present disclosure may provide an easy-to-use tool to assess joint and muscle behaviors.

Embodiments of an Apparatus for Measuring and Assessing Limb Movement Properties The present disclosure describes embodiments of an apparatus for measuring and assessing limb movement properties.

Figure 4A:
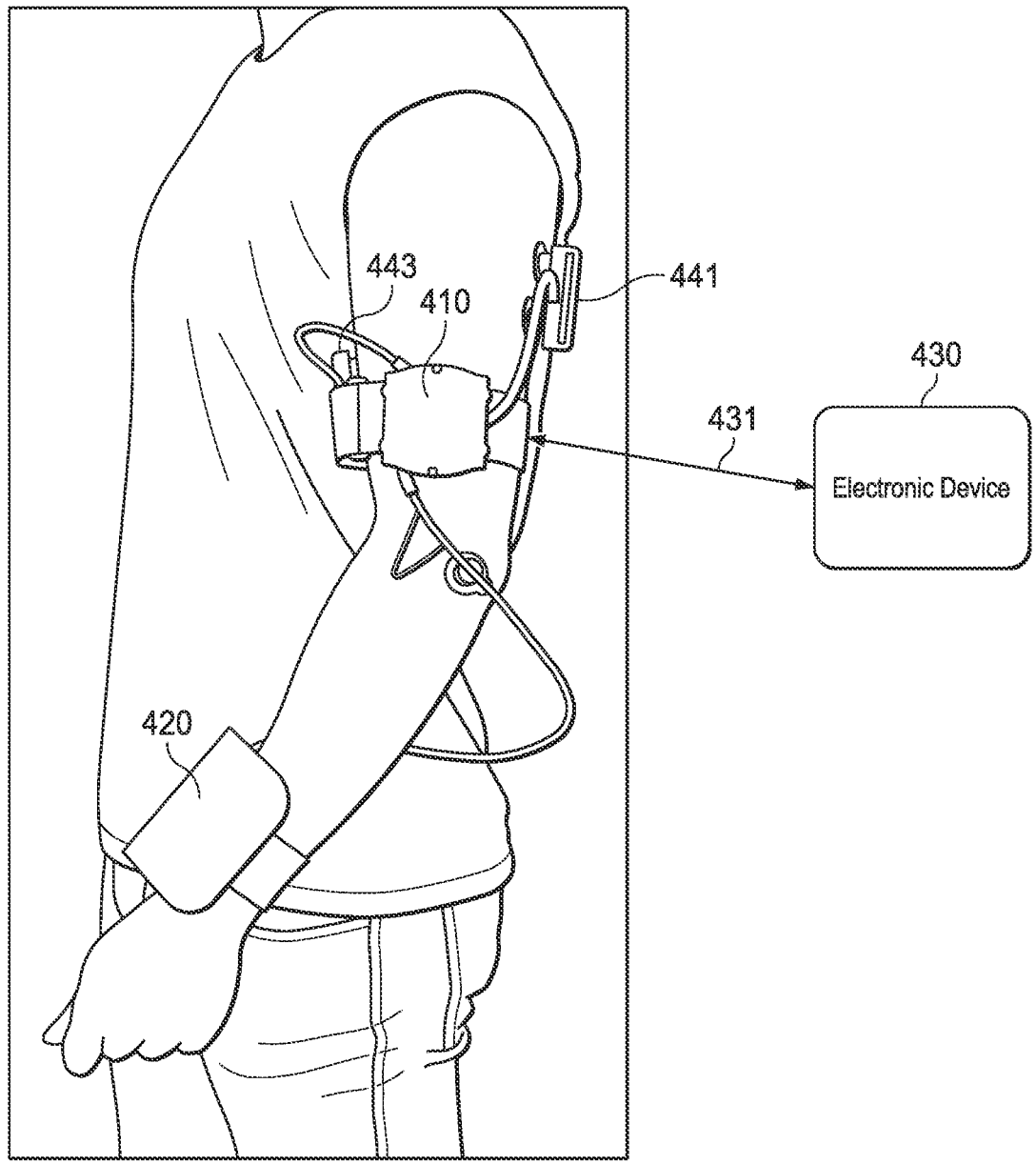
FIG. 4A describes the components of the PVRM modules.

Referring to FIG. 4A, the apparatus may include a PVRM, which may include one main module 410 (also referred as primary module), one moving module 420 (also referred as secondary module), and/or optionally one or more surface electromyographic (sEMG) sensors (441 and 443). The main module may electrically connect to the moving module and may be in communication with the moving module via wired communication or wireless communication. The main module may electrically connect to the sEMG and may be in communication with the sEMG via wired communication or wireless communication. In one implementation, a signal strength of EMG may correspond to a muscle activity. When the signal strength of EMG is below a certain pre-determined threshold, the muscle activity is low and may correspond to a relaxed state (also referred as passive state). When the signal strength of EMG is above the pre-determined threshold, the muscle may be in a active state. The apparatus may monitor whether a signal strength of EMG is below the pre-determined threshold so as to monitor whether the muscle is in a relaxed state.

Figure 4B:
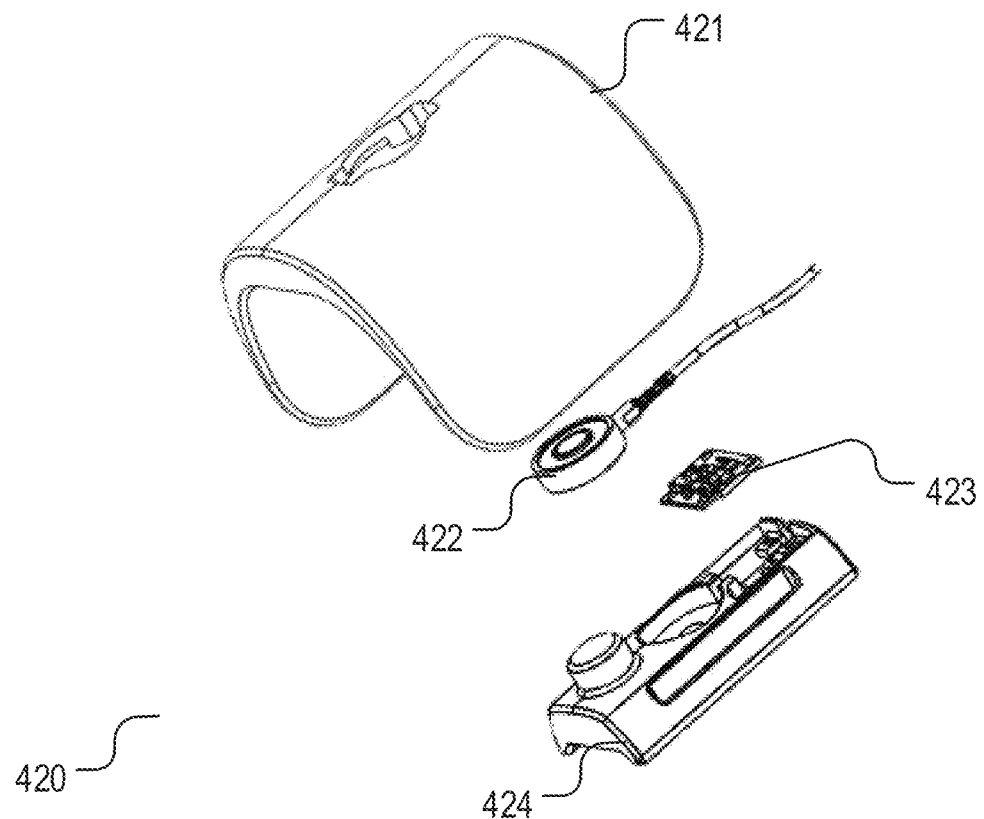
FIG. 4B describes the breakdown of the moving module.

Referring to FIG. 4B, the moving module 420 may include a load sensing sensor 422 (e.g., a load cell), angular/velocity sensor 423 (e.g., an inertial measurement unit (IMU)), a cover plate 421 to transfer applied load, and a housing 424 for packaging reasons. The moving module 420 may be attached at the patient's moving body segment. For example, when examining the biceps or triceps muscle, the moving module 420 is placed on the patient's forearm (e.g., on or near the wrist). The moving module 420 needs to remain in the same location and cannot be moved relative to the body segment once it is secured on the body. There may be no moving, shifting, or rotating between the moving module 420 and the body segment. In another implementation, the load sensing sensor 422 may be placed outside the moving module 420, for example, in a hand of a clinician, so as to measure the force exerted by the clinician.

Figure 4C:
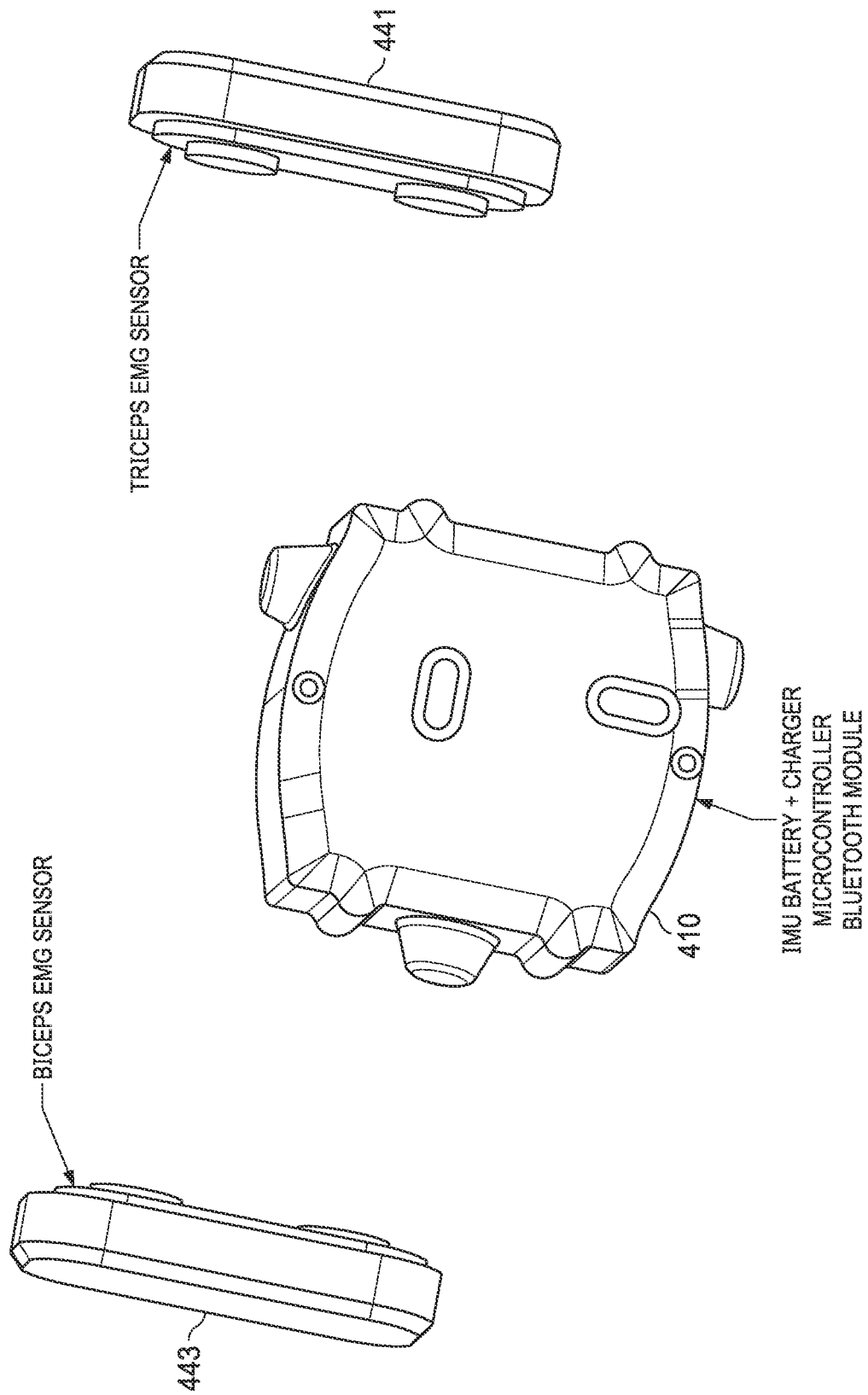
FIG. 4C describes the breakdown of the main module.

Referring to FIG. 4C, the main module 410 may include one or more of the following: an IMU, a battery (e.g. lithium polymer battery), a charger, a wired connection, a wireless transmitter, a microcontroller that receives the raw sensor data from the moving module and/or sends the data to an electric device (e.g., a remote tablet or a computer). The wireless transmitter may include a Bluetooth module. The main module 410 may be disposed on the stationary body segment. For example, when examining upper-arm muscles, the main module may be placed at a midpoint of the upper-arm.

The main and/or moving modules may have adjustable Velcro straps to accommodate body segments with different geometry and sizes. The sEMG electrodes may include one EMG 443 detecting flexor-muscle group (e.g., biceps) and one EMG 441 detecting extensor-muscle group (e.g., triceps) to monitor the muscle activity in the relevant paired antagonistic muscle groups. In one implementation, the sEMG sensors may include rigid electrodes with custom-housings and off-the-shell sensor pads. In other implementations, sEMG sensors may include other forms and/or other types, for example but not limited to cloth-based sensors and flexible-stretchable electronic sensors.

In one implementation, a reference electrode may be embedded inside or outside of the main module to provide ground for the EMG measurement.

In one implementation, the apparatus may include one main/primary module and two moving/secondary modules, such that the secondary modules are placed on body segments that are immediately proximal and distal to the body segment that contains the primary module. For example but not limited to, one primary module may be disposed on the midpoint of a body segment (e.g., upper arm), a first secondary module may be disposed at the forearm near the wrist of the subject, and a second secondary module may be disposed on the torso of the subject near the shoulder.

Referring to FIG. 4A, the apparatus may include an electronic device 430 (e.g., a remote PC or tablet) and the electronic device 430 is in communication 431 with the main module 410. The PVRM may transmits the measured raw data (angular position, speed, load, and EMG) to the electronic device 430 via wired or wireless communication.

Figure 5:
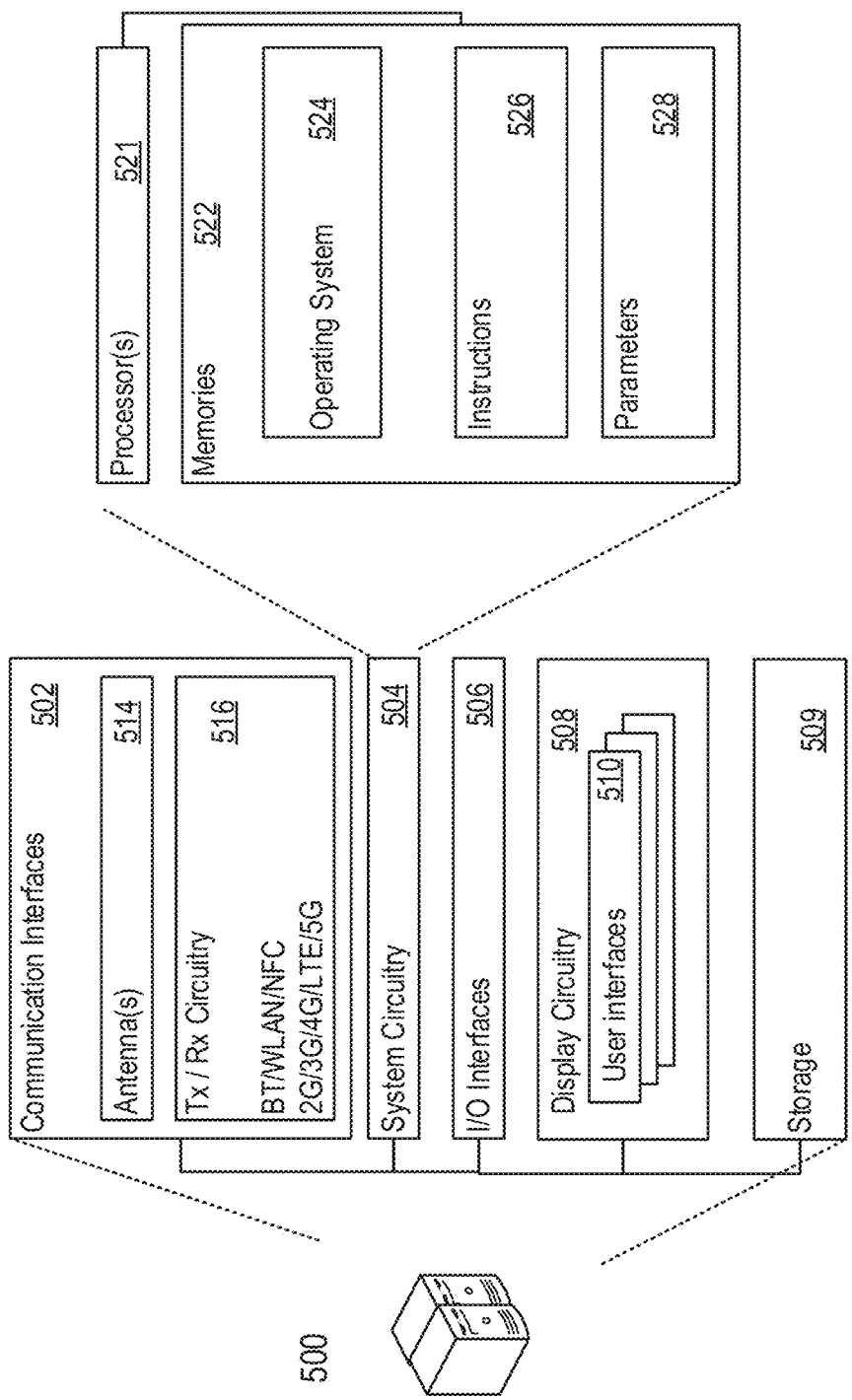
FIG. 5 shows an electronic device that may be used to implement one or more embodiments.

FIG. 5 shows an exemplary computer system for implementing the electronic device, which may receive the measured raw data and process the measured raw data. The electronic device 500 may be a computer terminal, a server, or a mobile device (e.g., a smart phone or a tablet). The electronic device 500 may include communication interfaces 502, a system circuitry 504, an input/output interfaces (I/O) 506, a display circuitry 508, and a storage 509. The display circuitry may include a user interface 510. The system circuitry 504 may include any combination of hardware, software, firmware, or other logic/circuitry. The system circuitry 504 may be implemented, for example, with one or more systems on a chip (SoC), application specific integrated circuits (ASIC), discrete analog and digital circuits, and other circuitry. The system circuitry 504 may be a part of the implementation of any desired functionality in the electronic device 500. In that regard, the system circuitry 504 may include logic that facilitates, as examples, running applications; accepting user inputs; saving and retrieving application data; establishing, maintaining, and terminating data connections for, as one example, internet connectivity; establishing, maintaining, and terminating wireless network connections, Bluetooth connections, or other connections; and displaying relevant information on the user interface 510. The user interface 510 and the inputs/output (I/O) interfaces 506 may include a graphical user interface, touch sensitive display, haptic feedback or other haptic output, voice or facial recognition inputs, buttons, switches, speakers and other user interface elements. Additional examples of the I/O interfaces 506 may include microphones, video and still image cameras, temperature sensors, vibration sensors, rotation and orientation sensors, headset and microphone input/output jacks, Universal Serial Bus (USB) connectors, memory card slots, radiation sensors (e.g., IR sensors), and other types of inputs.

Referring to FIG. 5, the communication interfaces 502 may include a radio frequency (RF) transmit (Tx) and receive (Rx) circuitry 516 which handles transmission and reception of signals through one or more antennas 514. The communication interface 502 may include one or more transceivers. The transceivers may be wireless transceivers that include modulation/demodulation circuitry, digital to analog converters (DACs), shaping tables, analog to digital converters (ADCs), filters, waveform shapers, filters, preamplifiers, power amplifiers and/or other logic for transmitting and receiving through one or more antennas, or (for some devices) through a physical (e.g., wireline) medium. As one specific example, the communication interfaces 502 may include transceivers that support transmission and reception under the Bluetooth (BT), wireless local area network (WLAN), near-field communication (NFC), 2G, 3G, BT, WiFi, Universal Mobile Telecommunications System (UMTS), High Speed Packet Access (HSPA)+, 4G/Long Term Evolution (LTE), and 5G standards.

Referring to FIG. 5, the system circuitry 504 may include one or more processors 521 and memories 522. The memory 522 stores, for example, an operating system 524, instructions 526, and parameters 528. The processor 521 is configured to execute the instructions 526 to carry out desired functionality for the electronic device 500. The parameters 528 may provide and specify configuration and operating options for the instructions 526. The memory 522 may also store any BT, WiFi, 3G, 4G, 5G or other data that the electronic device 500 will send, or has received, through the communication interfaces 502. In various implementations, a system power for the electronic device 500 may be supplied by a power storage device, such as a battery or a transformer.

In one implementation, the electronic device 500 may store instructions in its memory, and when the processor executes the instructions, the processor may be configured to cause the electronic device to perform receiving raw data by a PVRM, processing raw data to obtain processed data, processing the processed data to obtain a set of parameters; and obtaining a classification result based on the set of the parameters according to a classification algorithm. When the processor executes the instructions, the processor may also be configured to cause the electronic device to display, record, store any raw data, processed data, parameters, and/or final result at a local storage (e.g., hard drive), and/or transmit any raw data, processed data, parameters, and/or final result to be stored at a remote storage (e.g., a data server or an on-line cloud storage service).

Embodiments of a Method for Measuring and Assessing Limb Movement Properties

The present disclosure describes embodiments of a method for measuring and assessing limb movement properties.

Referring to FIG. 6A, a method 600 for measuring and assessing limb movement properties may include one or more of the following steps.

Step 610: conducting a test protocol with a PVRM. In one implementation, the PVRM may be disposed on a relevant limb of a subject. The subject may include a patient or a subject who is suspected to have a certain joint/muscle condition. In another implementation, the step 610 may include a calibration step to calibrate the PVRM.

Step 620: obtaining raw data quantifying the passive or active movement as well as patient information. In one implementation, the raw data may be collected by the PVRM, and then be transmitted to an electronic device from the PVRM.

Step 630: processing the raw data to obtain processed data. In one implementation, when the electronic device receives the raw data, the electronic device may process the raw data to obtain the processed data.

Step 640: obtaining a set of parameters based on the processed data. In one implementation, the electronic device may calculate the set of parameters based on the processed data. The set of parameters may include one or more key outcome parameters that describe the patient muscle condition.

Step 650: obtaining a classification result according to a classifying algorithm based on the set of parameters. In one implementation, the classification result may determine the type and degree of severity of the muscle/limb movement properties. The classification result of a history of the patient's muscle/joint behavior may be recorded. Step 650 may further include assessing a limb movement property according to the classification result.

Optionally, step 660: displaying and recording the set of parameters. In one implementation, data of a history of the patient's muscle/joint behavior may be recorded.

In one implementation, the method 600 may include step 650 but may not include step 660. In another implementation, the method 600 may include both the step 650 and step 660.

In one implementation, the method may comprise measuring and assessing conditions of elbow joints wherein the PVRM modules are disposed on the upper arm and forearm. In another implementation, the method may comprise measuring and assessing conditions of other joints wherein the PVRM modules may be modified slightly to be disposed on places of the subject. In another implementation, the method may measure and assess both flexor and extensor muscle groups.

The method may serve as a general method of assessing muscle/joint behavior for different patient populations. For example but not limited to, the method may be applied to quantify muscle disorder for patients with spasticity or rigidity or to quantify muscle strength for patients who underwent orthopedic surgery.

Figure 7:
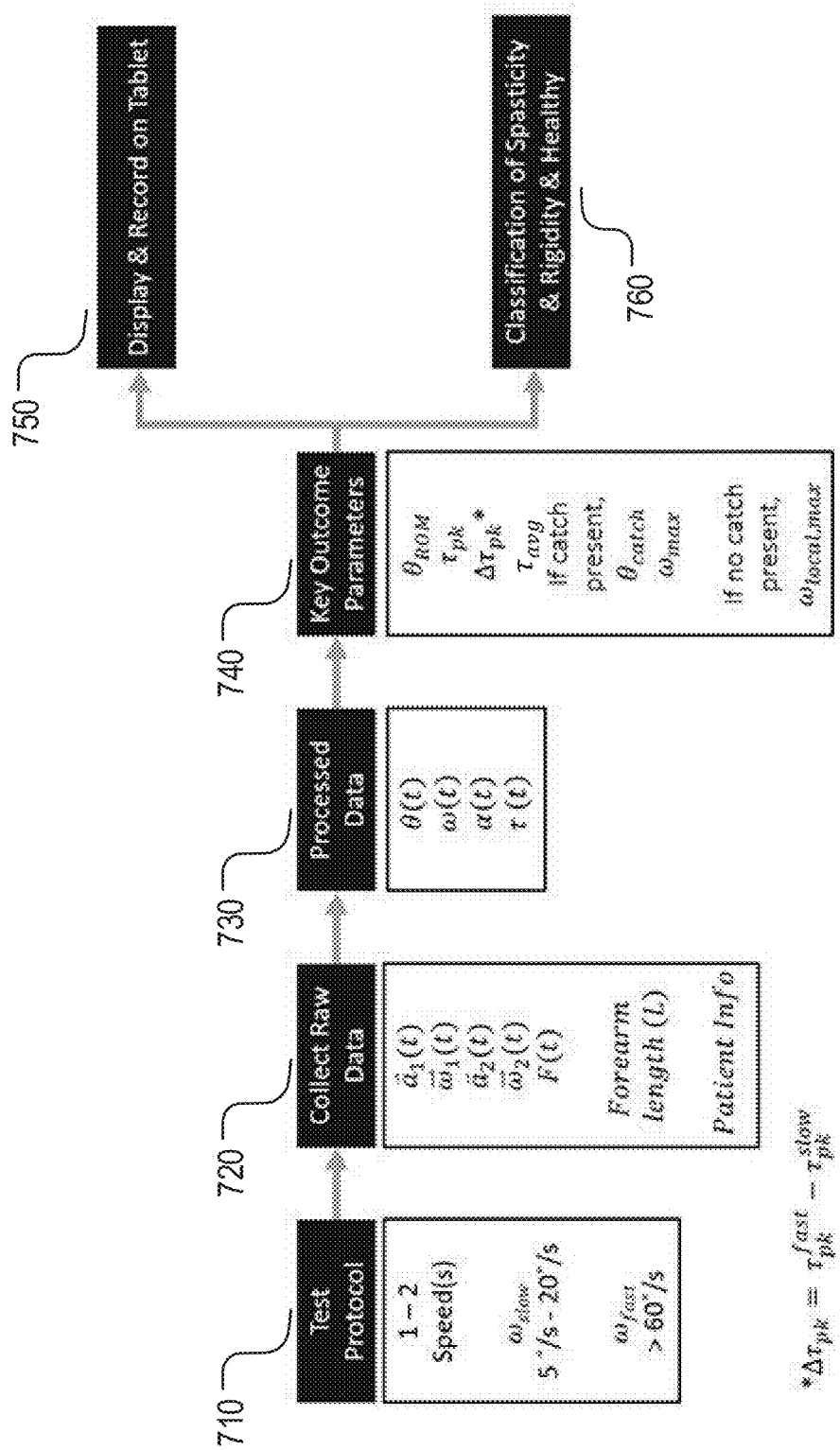
FIG. 7 describes a flow chart of parameters being computed for each step of the method.

In one implementation, referring to FIG. 7, for a subject who is suspected to have spasticity and/or rigidity conditions, a clinician may move the body segment of the subject wearing the PVRM modules at slow and fast speeds 710. For example but not limited to, a slow speed may refer to a maximum speed of between 5°/second and 20°/second, inclusive; a fast speed may refer to a maximum speed greater than than 60°/second.

During the passive joint movements, the PVRM collects the raw data 720, including acceleration and gyroscopic values, from inertial measurement units (IMU's) and patient information and transmit the raw data to an electronic device, for example but not limited to, a computer or a tablet. The electronic device may process the raw data to obtain processed data 730, including joint angular position ($\theta$), speed ($\dot{\theta}$), acceleration ($\ddot{\theta}$), and torque ($\tau$). The set of parameters including key outcome parameters 740 that identify characteristics of the muscle condition are computed. These parameters may include range of motion ($\theta_{ROM}$), peak muscle resistance ($\tau_{pk}$), change in peak muscle resistance at different speeds ($\Delta\tau_{pk}$), average muscle resistance ($\tau_{avg}$), catch angle ($\theta_{catch}$) (if catch present), max stretch speed before catch ($\omega_{max}$) (if catch present), or local max speed during acceleration of the body segment ($\omega_{local}$, max) (if catch is not present). The key outcome parameters are displayed/recorded on the tablet for the clinician and patient to monitor the history of the patient's muscle condition 750. A classification algorithm identifies the type (spasticity vs. rigidity) and degree (MAS 1-4 or UPDRS 1-4) of abnormal muscle condition using the raw PVRM data 760. The abnormal muscle condition is tracked during their treatment plans.

The method may be applicable to other patient populations. In some implementation, as the application differs, the testing protocol, key outcome parameters, and classifying algorithm changes to analyze different muscle tone and joint movement.

Referring to step 610, in one implementation, the patient may wear the PVRM and the clinician may exert force on the PVRM moving module over the load cell section. In another implementation, a clinician may passively move the body segment via the moving module. In another implementation, the patient may actively try to move the body segment while the clinician resists the movement via the moving module.

The PVRM collects the raw data from its sensors during the passive manipulation of the body segment by the clinician or the activation of the muscles by the patient. Depending on the application and patient population, the clinician may perform multiple movements at different speeds. For the spastic and rigid patient population, the clinician may passively move the body segment multiple times at both slow and fast speeds, since the difference in muscle behavior at slow and fast speeds may be used to classify the type of muscle disorder.

The method may include a step of calibrating the PVRM before conducting the test protocol. Before raw data is collected from the PVRM, a step of calibrating the IMUs and load cell may be conducted, for example but not limited to, a five-second calibration trial. The calibration may zero the load cell readings, and define a global coordinate frame, as the reference frame of IMUs may be misaligned about the respective y-axes (direction of gravity) due to the absence of magnetometers in these IMUs.

Referring to step 620, PVRM may collect raw data and transmit the raw data to an electronic device. The raw data may include two sets of 3-axis acceleration and gyroscopic readings from the two inertial measurement units (IMU's) of the moving and main modules, as well as the force readings from the load cell. These raw data may be used to quantify the biomechanical behavior such as joint position, velocity, acceleration, resistance, and stiffness during the body segment movement. The raw data may be transmitted to the electronic device via wireless or wired communication.

Optionally, some other raw data may be collected via other means. For example, forearm length (L) of the patient may be measured by a clinician using a ruler or a tape measure; and patient information may be collected via a questionnaire. The patient information may include one or more of the following types: age, gender, address, occupation, symptom, etc. These raw data may be input into the electronic device by typing with a keyword, with a touch screen, or by a voice-to-text recognition.

Referring to step 630, when the raw data are received by the electronic device (e.g., tablet or computer), the raw data are processed to calculate and obtain processed data. The processed data may include biomechanical data, for example but not limited to, sampled time, joint angle ($\theta$), joint velocity ($\omega$), joint acceleration ($\alpha$), and resistance ($\tau$).

In one implementation, the joint angle may be obtained by first calculating the 3D vectors of the IMUs of the moving and main module from the raw data and finding the relative angle between the two vectors using the dot product. In another implementation, the joint angle may be calculated by integrating gyroscopic values measured from the IMUs. Detailed steps of computing the 3D vectors will be discussed below.

The joint velocity may be obtained directly from the gyroscopic measurements from the IMUs.

The joint angular acceleration may be calculated differentiating the joint velocity data using Newton's method. The muscle resistance or strength may be expressed as torque (=measured load×moment arm) about the relevant joint. The inertial and gravitational effect of the moving body segment may be removed so that only the torque from the muscle is calculated.

The biomechanical data may be filtered to remove unwanted noise from motion artifacts or electrical noise. The angular position & speed (kinematic) data may be obtained from the IMU's and filtered at 100 Hz. The muscle resistance/strength and muscle activity may be filtered at 10 Hz and 100 Hz, respectively, using a 4th order Butterworth low pass filter. The muscle activity may be determined as "active" if the EMG signal is above a certain threshold (predefined patient-specific) for more than 1 second. Otherwise, muscle activity is determined as "passive." If the muscles are active, the test is repeated for examinations such as MAS or UPDRS that require the muscles to be relaxed (i.e., passive).

Referring to step 640, a set of parameters may include key outcome parameters that identify characteristics of the muscle condition. The set of parameters may include one or more of the following: range of motion ($\theta_{ROM}$), peak muscle resistance ($\tau_{pk}$), change in peak muscle resistance at different speeds ($\Delta\tau_{pk}$), average muscle resistance ($\tau_{avg}$), catch angle ($\theta_{catch}$) (if catch present), max stretch speed before catch ($\omega_{max}$) (if catch present), or local max speed during acceleration of the body segment ($\omega_{local,max}$) (if catch is not present). The method of calculating the set of parameter is discussed in details below.

Referring to step 650, a classifying algorithm may be modified depending on the application of the general method. In one implementation, when the method is used for assessing abnormal muscle conditions such as spasticity and rigidity, the algorithm may analyze key outcome metrics related to spasticity and rigidity such as peak muscle resistance ($\tau_{pk}$), changes of peak resistance between slow and fast stretch speed ($\Delta\tau_{pk}$), average muscle resistance (Tavg), range of motion ($\theta_{ROM}$), and stretch speed ($\omega$).

Figure 6B:
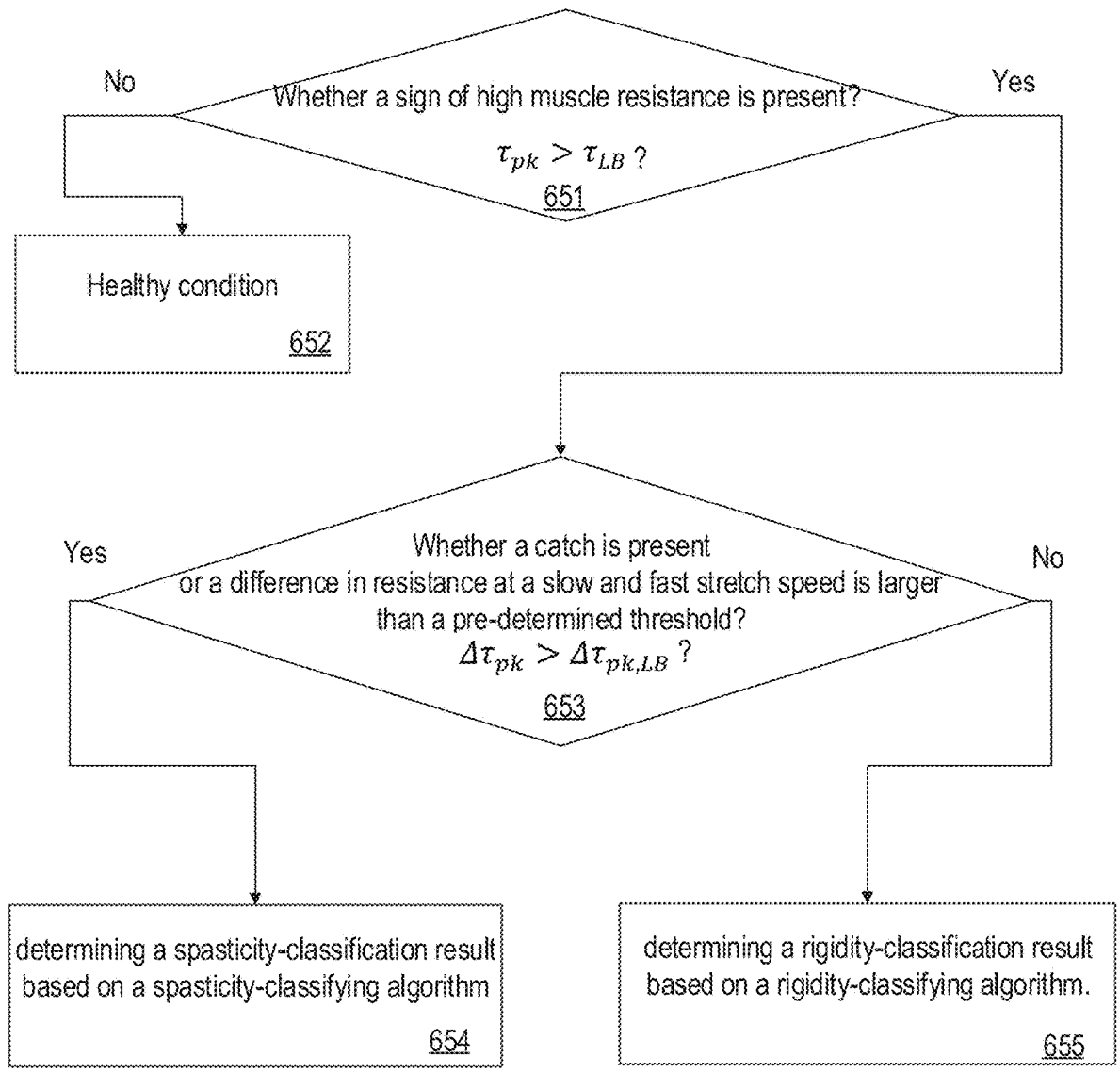
FIG. 6B describes a flow chart of a method of classifying different types of muscle tone.

Referring to FIG. 6B, the step 650 may include one or more the following steps:

Step 651: determining whether a sign of high muscle resistance is present based on the set of parameters. The first level of classification starts by searching for signs of high muscle resistance ($\tau_{pk} > \tau_{LB}$). Healthy muscles do not show high muscle resistance. When $\tau_{pk}$ is larger than a pre-determined threshold $\tau_{LB}$, the sign of high muscle resistance is present. When $\tau_{pk}$ is not larger than the pre-determined threshold $\tau_{LB}$, the sign of high muscle resistance is not present.

Step 652: in response to determining that the sign of high muscle resistance is not present, determining a subject is in a healthy condition.

In response to determining that a sign of high muscle resistance is present, the step 650 may include step 653: determining whether a catch is present or the difference in resistance at slow and fast stretch speed is larger than a pre-determined threshold; step 654: in response to determining that the catch is present or the difference in resistance at slow and fast stretch speed is larger than a pre-determined threshold, determining a spasticity-classification result based on a spasticity-classifying algorithm; and step 655: in response to determining that the catch is not present and the difference in resistance at slow and fast stretch speed is not larger than the pre-determined threshold, determining a rigidity-classification result based on a rigidity-classifying algorithm.

The first level of classification starts by searching for signs of high muscle resistance ($\tau_{pk} > \tau_{LB}$). Healthy muscles do not show high muscle resistance. If high resistance is observed, the muscle may be spastic if a catch is present or the difference in resistance at slow and fast stretch speed is large enough ($\Delta\tau_{pk} > \Delta\tau_{pk,\,LB}$). Otherwise, the muscle tone is considered to be displaying rigidity.

Spasticity may be categorized into different levels depending on the severity according to a spasticity-classifying algorithm, so as to obtain a spasticity-classification result. In one implementation, the spasticity-classifying algorithm may include a defined Metric of Spasticity (MOS):

$$MOS = (a \times \tau_{pk}) + (b \times \Delta\tau_{pk}) + (c \times \tau_{avg}) + (d \times \theta_{ROM}) + (e \times \theta_{catch})$$

wherein a, b, c, d, and e are constants; a, b, c>0 and d, e<0; and |a|>|b|>|c|>|d|>|e|. MOS may be a weighted metric that quantifies the severity of spasticity by assigning different weights to the contributing factors to spasticity such as peak resistance, change in peak resistance at different speeds, range of motion, and catch angle.

In one implementation, values of |a|, |b|, |c|, |d|, |e| may be patient-specific and/or disease-specific, and a severity of spasticity may be positively correlated with the value of MOS.

Figure 8A:
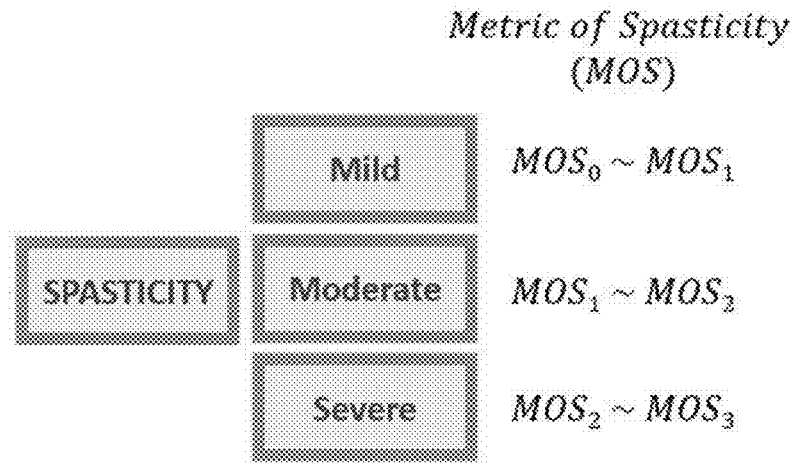
FIG. 8A describes the breakdown of different levels of spasticity (type of muscle tone).

In another implementation, a lookup table including series of ranges to determine the severity of spasticity. For one example, referring to FIG. 8A, the lookup table may include three ranges (from $MOS_0$ to $MOS_1$, from $MOS_1$ to $MOS_2$, and from $MOS_2$ to $MOS_3$) corresponding to severity levels of spasticity including mild, moderate and severe. For another example, the lookup table may include six ranges, corresponding to severity levels of spasticity from 0 to 5. The lookup table including six ranges matches the MAS score of ranging from 0 to 5), so as to be easily adapted by the medical community. The calculated value of MOS may be compared to the lookup table and determine the spasticity-classification result based on the lookup table and the value of MOS.

Rigidity may be categorized into different levels of severity depending on the severity according to a rigidity-classifying algorithm, so as to obtain a rigidity-classification result. In one implementation, the rigidity-classifying algorithm may include a defined Metric of Rigidity (MOR):

$$MOR = (a \times \tau_{avg}) + (b \times \tau_{pk})$$

wherein a, b are constants; and a, b>0. MOR may be a weighted metric that quantifies the severity of rigidity by assigning different weights to the contributing factors to rigidity such as peak muscle resistance and average muscle resistance.

In one implementation, values of |a|, |b| may be patient-specific and/or disease-specific, and a severity of spasticity may be positively correlated with the value of MOR.

Figure 8B:
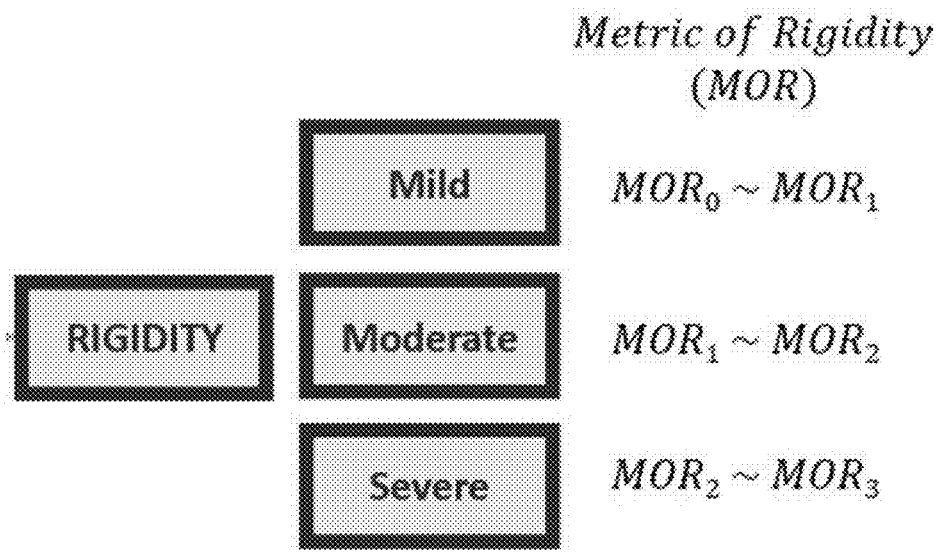
FIG. 8B describes the breakdown of different levels of rigidity (type of muscle tone).

In another implementation, a lookup table including series of ranges to determine the severity of rigidity. For one example, referring to FIG. 8B, the lookup table may include three ranges (from $MOR_0$ to $MOR_1$, from $MOR_1$ to $MOR_2$, and from $MOR_2$ to $MOR_3$) corresponding to severity levels of rigidity including mild, moderate and severe. For another example, the lookup table may include five ranges, corresponding to severity levels of rigidity from 0 to 4. The lookup table including five ranges match the UPDRS scores ranging from 0 to 4, so as to be easily adapted by the medical community. The calculated value of MOR may be compared to the lookup table and determine the rigidity-classification result based on the lookup table and the value of MOR.

In another embodiment, when the method is used for assessing muscle strength, an algorithm may depend on parameters such as muscle strength ($\tau_s$) and ROM. This algorithm's parameters may vary and depend on the relevant muscle group and profile of the patient, which includes but not limited to gender, weight, fitness level, etc.

Figure 9:
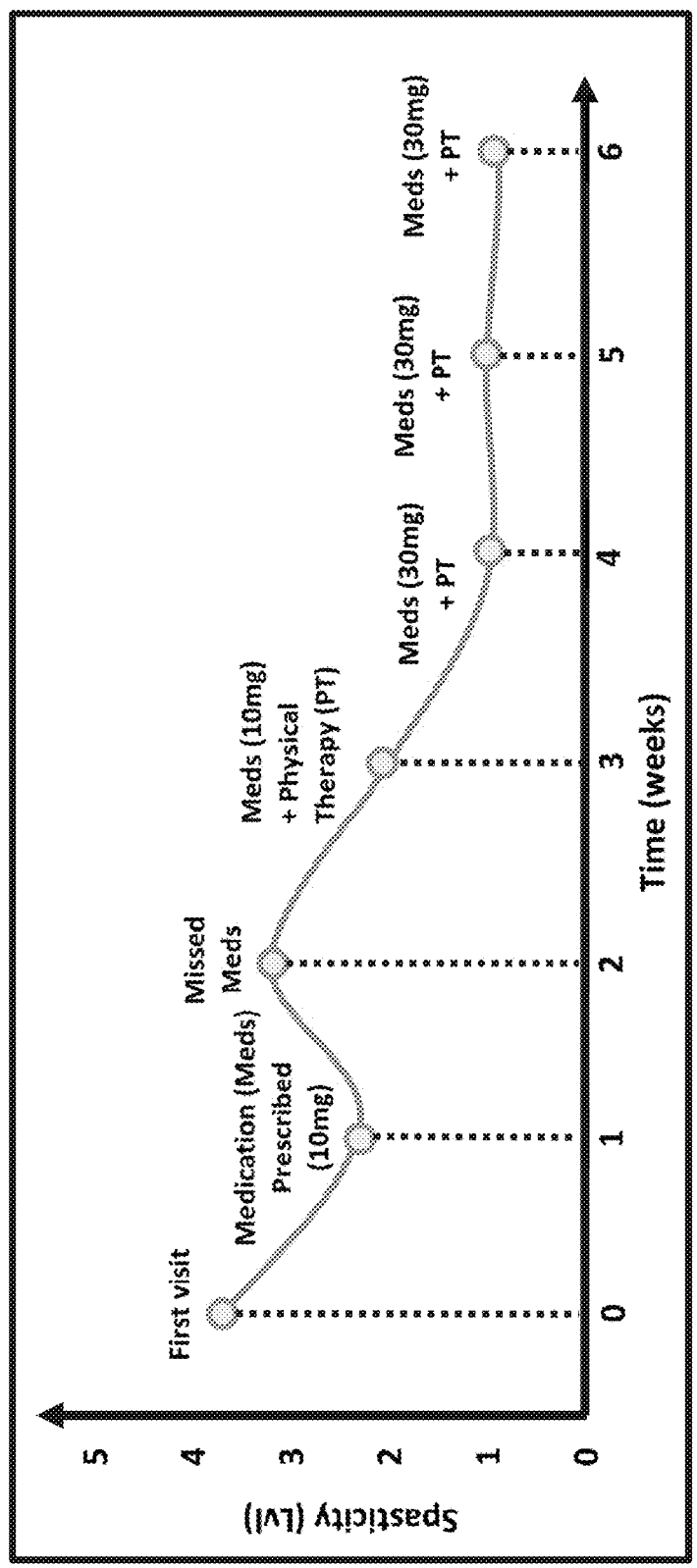
FIG. 9 describes a chart showing a progression of a limb muscles behavior/conditions.

Referring to step 660, for a patient, the method may store and keep track of the muscle and joint behavior from previous patient visits to observe the progression or regression of the muscle and/or joints. In one implementation, key information/note may be added for each assessment such as the treatment information (timing/type/intensity) or major injuries. In another implementation, referring to FIG. 9, the tracking may be either tabulated or graphed to see the progression of the muscle/joint behavior/conditions.

Quantification of Spasticity and Rigidity

The biomechanical differences may exist between healthy, spastic, and rigid muscle tone.

Figure 10:
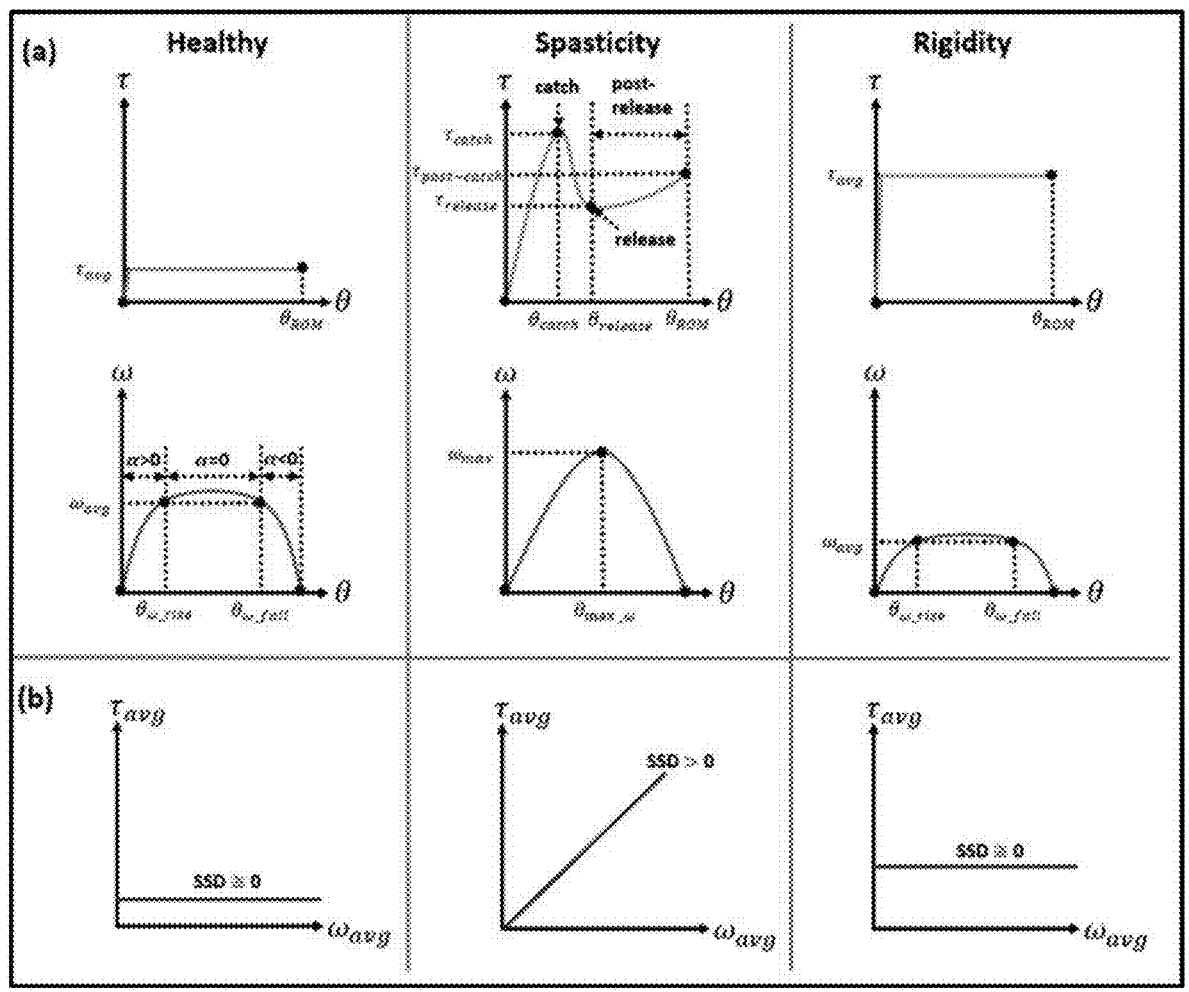
FIG. 10 describes a conceptual biomechanical comparison of healthy, spastic, and rigid arms.
Figure 11:
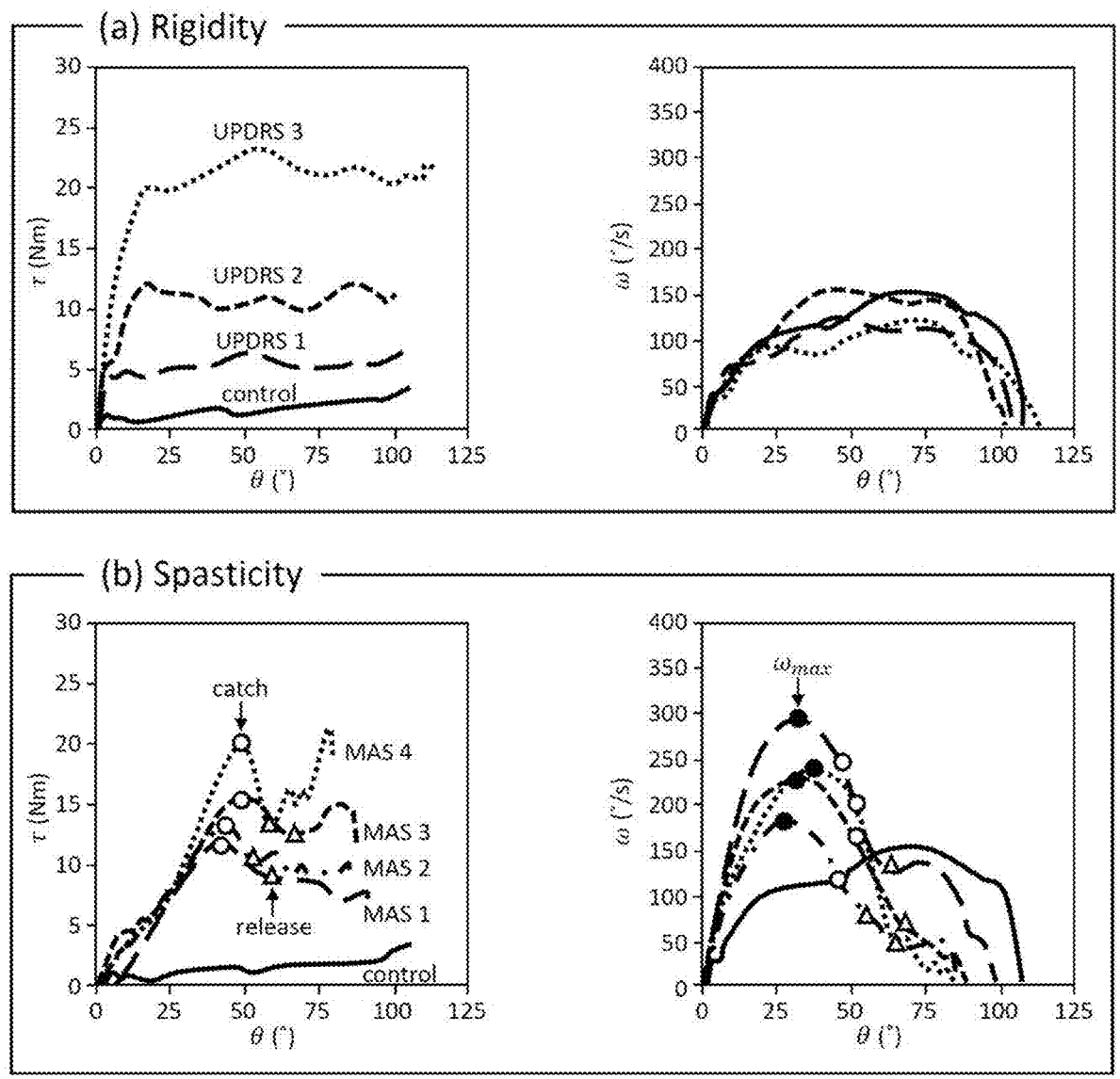
FIG. 11 shows biomechanical data of different degrees of rigid and spastic arms.

FIG. 10 shows conceptual biomechanical comparison of healthy, spastic, and rigid arms, including conceptual graphs comparing prototypical healthy, spastic, and rigid muscle behavior during passive movement at (a) clinician's preferred stretch speed in terms of muscle resistance ($\tau$) and stretch speed ($\omega$) as functions of joint angle ($\theta$), and (b) stretch speed dependency of muscle resistance (SSD). Key points (black circles) and parameters may be identified to characterize each muscle category. FIG. 11 shows biomechanical data of different degrees of rigid (a) and spastic (b) arms. For the spasticity data, the locations of catch (open circle), release (open triangle), and local maximum of w after release (filled circle) are shown.

Referring to FIGS. 10 and 11, for healthy muscles during passive movement, the muscle resistance may be low, since there is no abnormal muscle condition causing stiff muscle behavior. Referring to FIG. 10, the stretch speed profile may resemble a trapezoidal shape including acceleration, constant speed, and deceleration regions. Referring to FIG. 11, the stretch speed dependency of muscle resistance (SSD) may be non-existent, meaning that the muscle resistance remains the same regardless of stretch speed of the joint.

Referring to FIGS. 10 and 11, spasticity may exhibit high muscle resistance and presence of catch-release behavior during passive movement. A catch-release behavior may be defined as a sudden appearance of increased muscle activity during passive movement, and it may be a unique trait of spastic muscles.

Figure 12:
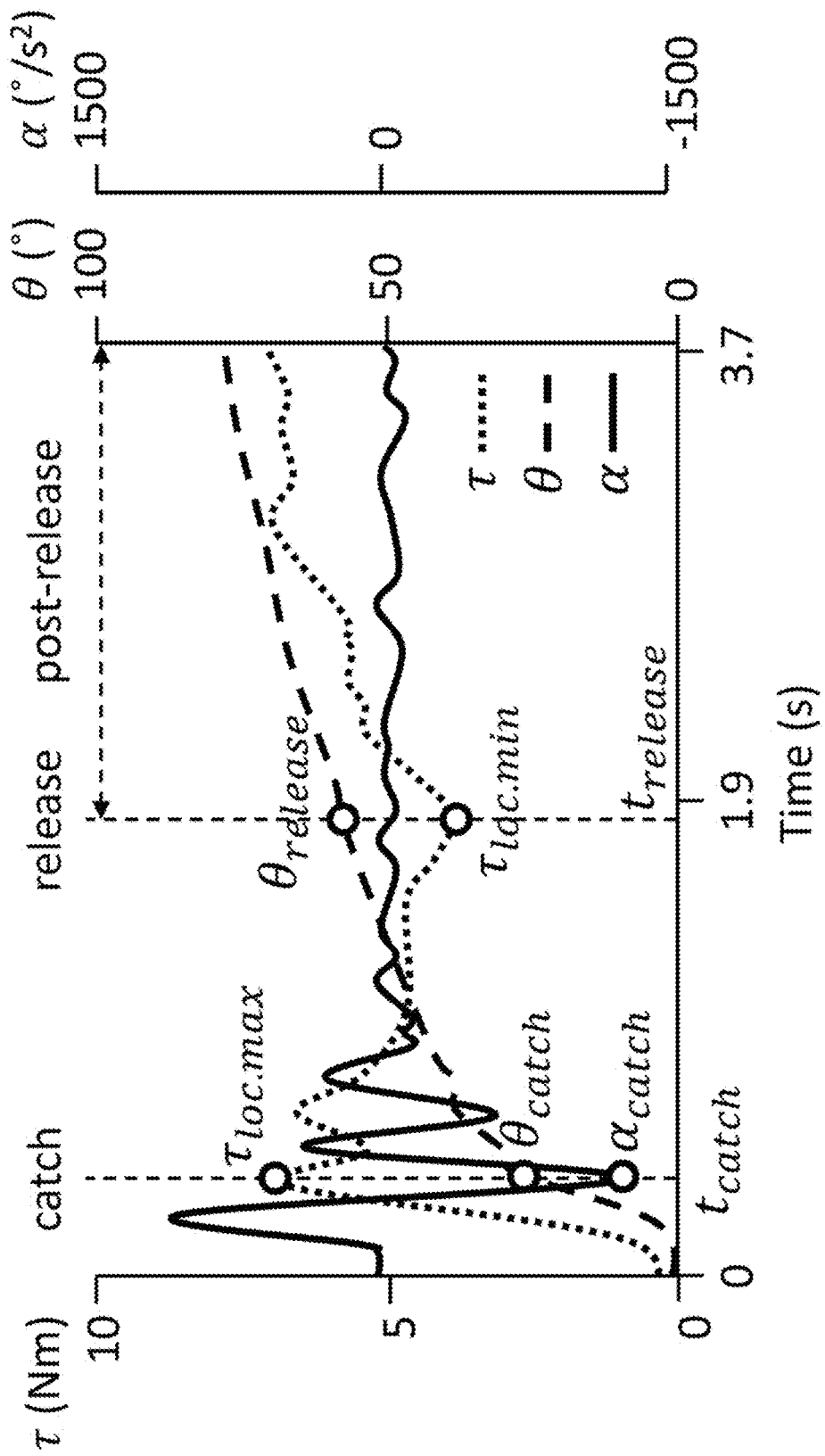
FIG. 12 shows a catch-release detection algorithm using biomechanical data.

FIG. 12 shows catch-release detection algorithm using biomechanical data. Catch may be defined by investigating the clinical definition of a catch: the catch may be defined as a sudden appearance of increased muscle activity in response to a fast passive stretch, which lead to an abrupt reduction in speed (1st criteria) and sudden increased resistance (2nd criteria) during the movement, at a certain angle before maximum range of motion (ROM) is reached (3rd criteria). A catch may be quantitatively defined as the instance when the following three criteria are met: 1) maximum deceleration of the arm, 2) the torque exceeding a threshold that may be trial specific (threshold=1.25× standard error of resistance during one trial) and peaking at a local maximum, and 3) the angular position is below 90% of the subject's maximum ROM. The release may be defined as the instance of the first local minimum of torque after catch.

Referring to FIG. 12, the quantitative definition and detection algorithm of the catch-release behavior is explained. The catch-release behavior may be not observed for every spasticity patient, since spasticity may change depending on the time of day, stress level, level of physical activity, etc.

Figure 13:
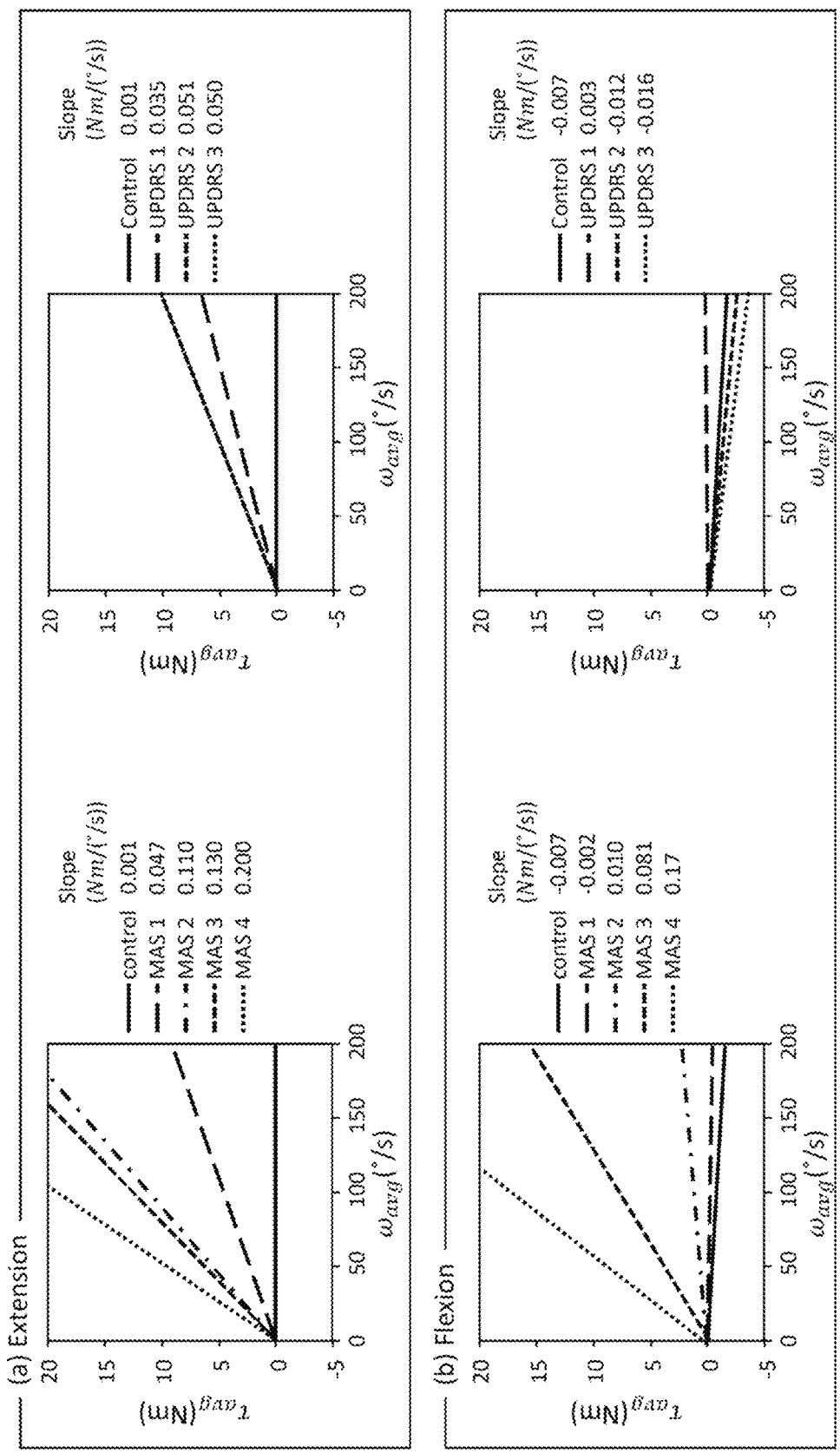
FIG. 13 shows a stretch speed dependency of applied torque.

FIG. 13 shows stretch speed dependency of applied torque (SSD) of control, spasticity, and rigidity in extension (Top) and flexion (Bottom), as generated from regression lines of the average resistance and stretch speed. A more positive slope (SSD) may indicate greater muscle resistance at faster stretch speeds.

Referring to FIG. 13, spasticity may be stretch speed dependent (SSD similar to Δτ_pk), meaning that the muscle resistance may increase at faster stretch speeds.

Referring to FIGS. 10 and 11, rigidity may demonstrate high muscle resistance but a constant muscle resistance profile (unlike spasticity) due to an absence of catch-release behavior during passive movement. Instead, the muscle resistance may be uniformly increased across the range of motion. Referring to FIG. 13, rigidity may be not dependent on stretch speed like spasticity, so the SSD may be near zero like healthy muscles. Referring to FIG. 11, more severe cases of spasticity may display higher muscle resistance, less range of motion, and more stretch speed dependency, while more severe cases of rigidity may display higher muscle resistance.

Calibration and Data Processing of the PVRM

Figure 14:
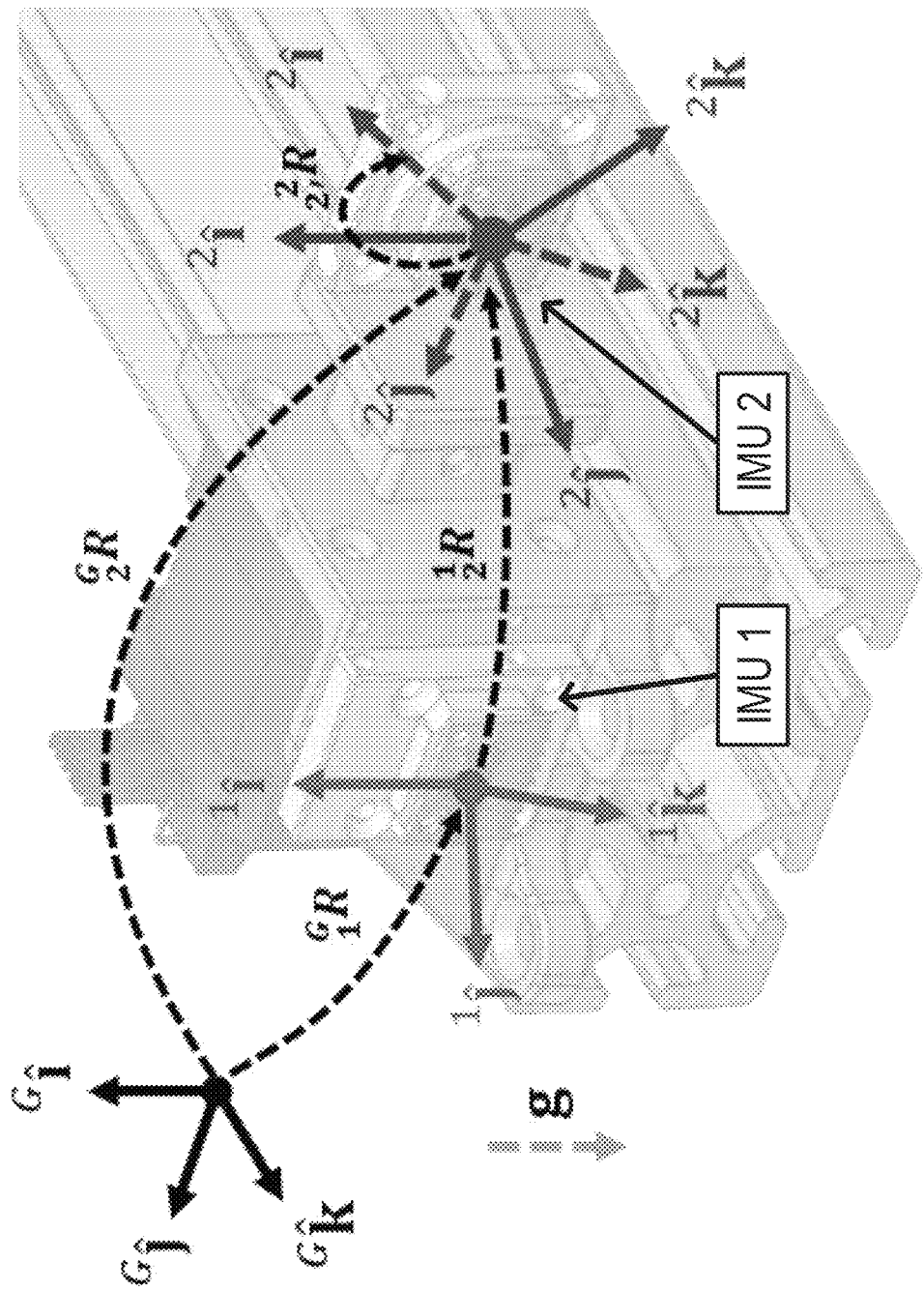
FIG. 14 shows the calibration procedure of the PVRM modules.

The joint angular position (θ) and velocity (ω) may be computed using the readings of the IMUs of the main module (IMU 1) and moving module (IMU 2) shown in FIG. 14. Each IMU outputted a unit quaternion vector (q) that contained four values (a, b, c, d, where a defines the amount of rotation and b, c, d defines the axis of rotation in the 3D Cartesian space) to quantify rotation relative to the reference frame of the IMU ($\hat{i}, \hat{j}, \hat{k}$) in Equation 1.

$$_B^A q = a + b_B{}^A\hat{i} + c\; \hat{a}_B{}^A\hat{j} + d_B{}^A\hat{k} \qquad \text{(Equation 1).}$$

Quaternion representation may be chosen over Euler angles due to quaternion's simple composition and absence of gimbal lock problems. The rotation matrixes of the IMUs ($_B^A R$) may be derived from the quaternion values of the IMUs ($\vec{q}_i$), using Equation 2. The notation of rotation matrixes may be used: $_B^A R$ is the rotation matrix that rotates frame {A} to frame {B}. Each column of the rotation matrix may contain orientations of the local x, y, and z-axes of the rotated IMU relative to its initial coordinate frame.

$$_B^A R = \begin{bmatrix} _B^A\hat{i} & _B^A\hat{j} & _B^A\hat{k} \end{bmatrix} = \begin{bmatrix} a^2+b^2-c^2-d^2 & 2bc-2ad & 2bd+2ac \\ 2bc+2ad & a^2-b^2+c^2-d^2 & 2cd-2ab \\ 2bd-2ac & 2cd+2ab & a^2-b^2-c^2+d^2 \end{bmatrix}. \qquad \text{(Equation 2)}$$

FIG. 14 shows a calibration of the PVRM: (a) illustrates the physical arrangement during calibration, and (b) represents the reference and coordinate frame of IMU 1 and 2 as well as the global reference frame.

Referring to FIG. 14, before any measurement data may be collected from the PVRM, a 5-second calibration trial for the IMUs and load cell may be conducted. The calibration may be used to 1) zero the load cell readings, and 2) define a global reference frame ({G}=$^G\hat{i}, ^G\hat{j}, ^G\hat{g}$), since reference frame of IMU 1 ({1}=$^1\hat{i}, ^1\hat{j}, ^1\hat{g}$) and IMU 2 ({2}=$^2\hat{i}, ^2\hat{j}, ^2\hat{g}$) may be misaligned about the respective y-axes (direction of gravity) due to the absence of magnetometers in these IMUs. In the calibration procedure, A global reference frame {G} may be defined by physically aligning the two modules (FIG. 14, light grey image). To compute the relative angular position between IMU 1 and 2, the global coordinate frame may be defined as the reference frame of IMU 1 since IMU 1 is mostly stationary during the arm movements. During the calibration process, the IMU and load cell data may be collected. The load cell may have no applied load. During the calibration process, the IMU data may be collected. A calibration matrix ($_2^1 R$) may be computed to align the reference frame of IMU 2 to reference frame of IMU 1 in Equation 3.

$$_2^1 R = {_1^G R}\, _2^G R^{-1} \qquad \text{(Equation 3).}$$

Figure 15:
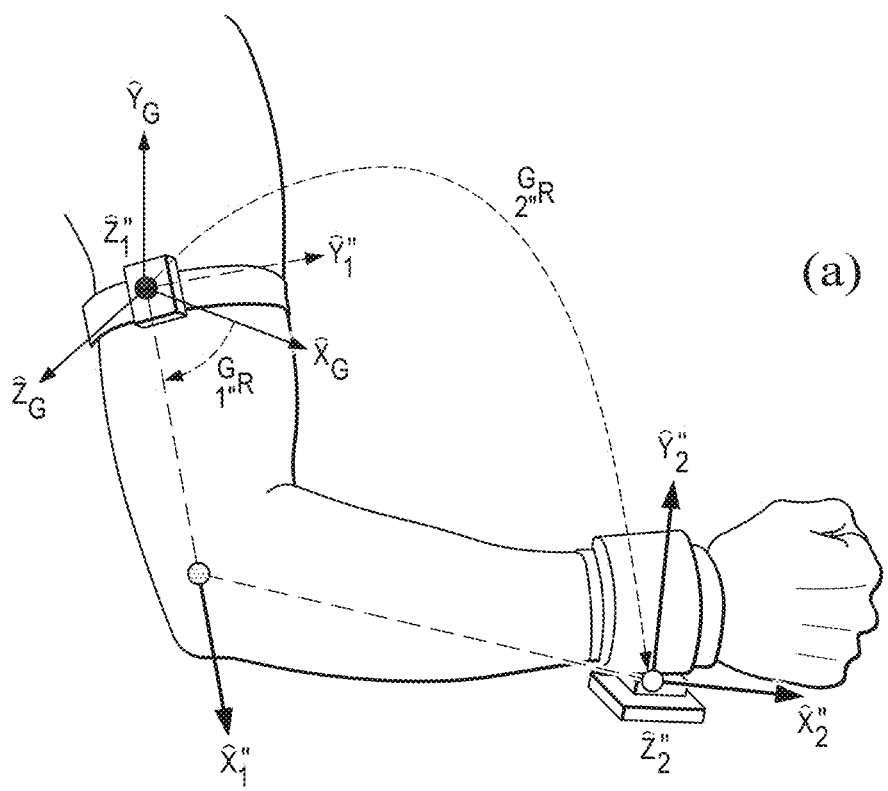
FIG. 15 shows a computation of rotation matrix and elbow joint angular position.
Figure 15:
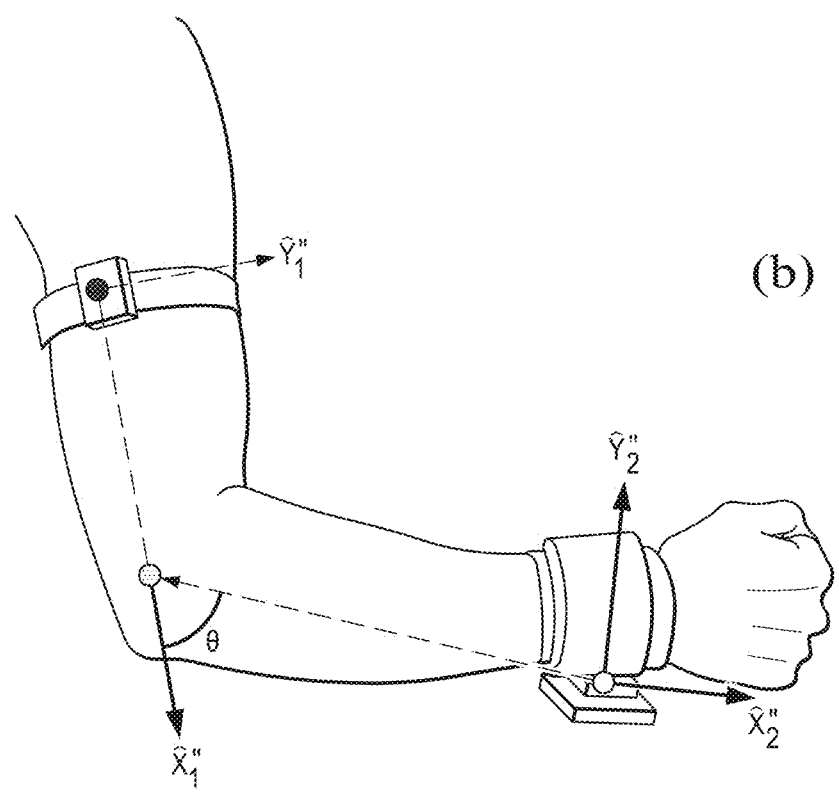

FIG. 15 shows computation of (a) rotation matrix of IMU 2 ($_2 {}^G R$) that may be referenced from the global frame and (b) of elbow joint angular position (θ).

During each calibration trial, the average of the calibration matrix for the 500-calibration data (5s×100 data/s) may be computed for obtaining a more accurate calibration matrix according to Equation 4.

$$R_c = \frac{\sum_{k=1}^{500} \frac{1}{2} R(k)}{500}. \qquad \text{(Equation 4)}$$

After the calibration, the relative orientation of IMU 2 ($_2{}^{1'} R$) with respect to reference frame of IMU 1 may be computed according to Equation 5. The single quotation mark after any frame may denote post calibration phase, whereas the absence of quotation mark may denote any frame during the calibration phase.

$$_2{}^{1'} R = R_c\, _2^2 R \qquad \text{(Equation 5).}$$

To obtain $\theta_{DMP}$, the angular difference between the reference unit vectors of IMU 1 and IMU 2 normal to the rotation axis may be computed using the dot product of the two vectors according to Equation 6, where, $\hat{u}$ is $\hat{i}, \hat{j}, \hat{k}$ for pitch, roll, and yaw, respectively.

$$\theta_{DMP} = \cos^{-1}\left( \frac{^{1'}\hat{u} \cdot {_{2'}}\hat{u}}{\|^{1'}\hat{u}\| \|_{2'}\hat{u}\|} \right). \qquad \text{(Equation 6)}$$

Data Processing of Muscle Resistance (τ)

Figure 16:
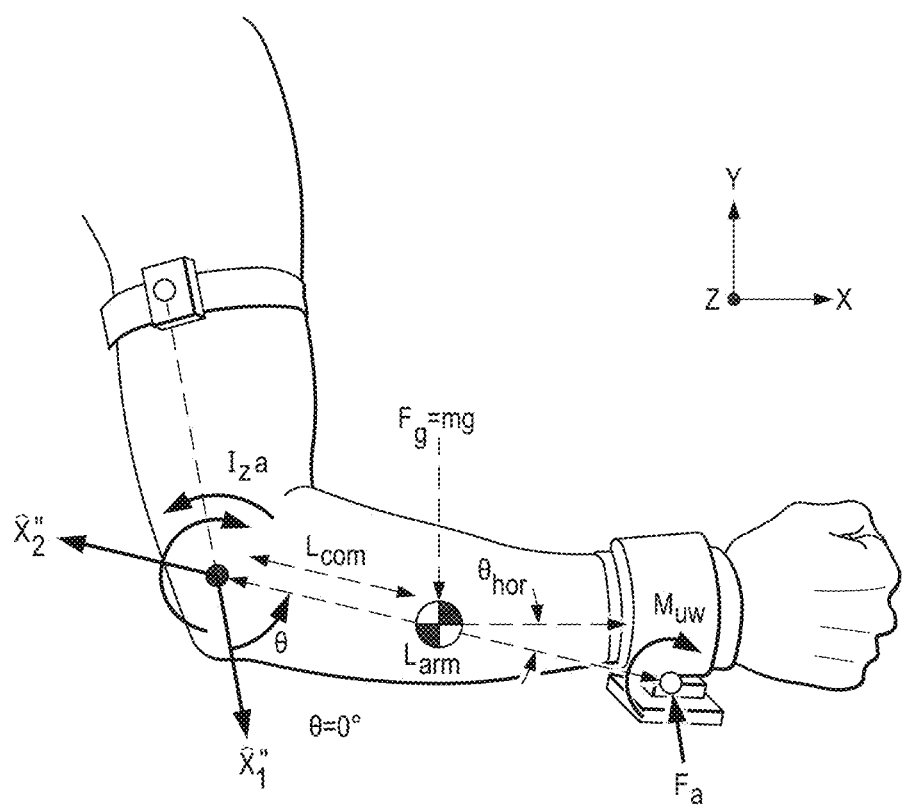
FIG. 16 shows a free-body diagram of a subject's arm during passive movement.

FIG. 16 shows a free-body diagram of a subject's arm during passive movement. θ=0° when the forearm is aligned to the upper arm. Calculated muscle resistance (τ) may have various contributions, including the torque due to the applied force of the clinician ($F_a L_{arm}$), inertial effect ($I_z \alpha$), gravitational effect ($F_g \cos(\theta_{hor}) L_{com}$), and/or unwanted moments ($M_{uw}$) due to tilting of the load cell. Equations 7 and 8 show the sum of moment about z-axis ($M_z$) and rearrangement of this equation for solving τ, respectively.

$$\Sigma M_z = I_z \alpha = F_a L_{forearm} - F_g \cos(\theta_{hor}) L_{com} - M_{uw} - \tau. \qquad \text{(Equation 7).}$$

$$\tau = F_a L_{forearm} - F_g \cos(\theta_{hor}) L_{com} - I_z \alpha - M_{uw}. \qquad \text{(Equation 8).}$$

$F_a$ and $L_{arm}$ may represent the applied force on the load cell and distance between elbow joint and load cell, respectively. $\alpha$, $F_g$, $\theta_{hor}$ are the angular acceleration, force due to gravity, and angle with the global x-axis, respectively. $L_{forearm}$ may represent a length of the forearm. The mass of moving body segment (forearm and hand) (m), distance from the elbow joint to the center of mass (COM) of the moving body segment ($L_{com}$), and rotational inertia of the moving body segment about the elbow joint or Z-axis ($I_z$) may be estimated using known anthropometric equations given the subject's gender, body mass, and height. A nine-point-moving-average filter may be used to filter the calculated t data.

While the particular disclosure has been described with reference to illustrative embodiments, this description is not meant to be limiting. Various modifications of the illustrative embodiments and additional embodiments of the disclosure will be apparent to one of ordinary skill in the art from this description. Those skilled in the art will readily recognize that these and various other modifications may be made to the exemplary embodiments, illustrated and described herein, without departing from the spirit and scope of the present disclosure. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

The invention claimed is:

1. A method for measuring and assessing limb movement properties, the method comprising:
    disposing a position, velocity, and resistance meter (PVRM) on one or more body segments connected by a joint of a subject;
    conducting a test protocol with the PVRM, wherein the test protocol comprises passive manipulation of the one or more body segments multiple times at different speeds;
    obtaining raw data from the PVRM and transmitting the raw data from the PVRM to an electronic device;
    processing the raw data to obtain processed data;
    obtaining a set of parameters based on the processed data;
    obtaining a classification result according to a muscle resistance-related classifying algorithm based on the set of parameters, by:
        determining whether a sign of high muscle resistance is present based on the set of parameters;
        in response to determining that the sign of high muscle resistance is not present, determining a subject is in a healthy condition; and
        in response to determining that the sign of high muscle resistance is present:
            determining whether a catch is present and/or a difference in resistance at a slow and fast stretch speed of the different speeds is larger than a pre-determined threshold,
            in response to determining that the catch is present and/or the difference in resistance at the slow and fast stretch speed is larger than the pre-determined threshold, determining a spasticity-classification result based on a spasticity-classifying algorithm, and
            in response to determining that the catch is not present and the difference in resistance at the slow and fast stretch speed is not larger than the pre-determined threshold, determining a rigidity-classification result based on a rigidity-classifying algorithm;
    assessing a limb movement property according to the classification result;
    reconstructing a history of the limb movement property for a treatment plan for the subject;
    generating a table or graph of the reconstructed history of the limb movement property for the treatment plan, wherein the treatment plan includes details of timing, type, and intensity of the test protocol conducted; and
    displaying the generated table or graph to show progression of muscle conditions under the treatment plan and displaying the treatment plan;
    wherein the spasticity-classifying algorithm comprises a defined Metric of Spasticity (MOS):

$$MOS=(a\times\tau_{pk})+(b\times\Delta\tau_{pk})+(c\times\tau_{avg})+(d\times\theta_{ROM})+(e\times\theta_{catch})$$

wherein:
    $\tau_{pk}$ is a peak muscle resistance;
    $\Delta\tau_{pk}$ is a change in peak muscle resistance at the different speeds;
    $\tau_{avg}$ is an average muscle resistance;
    $\theta_{ROM}$ is a range of motion;
    $\theta_{catch}$ is a catch angle;
    a, b, c, d, and e are constants;
    a>0, b>0, c>0, d<0, e<0; and
    |a|>|b|>|c|>|d|>|e|.

2. The method according to claim 1, wherein:
the raw data comprises a set of acceleration data, a set of rotation data, and a set of force data.

3. The method according to claim 2, wherein:
the raw data further comprises a forearm length and patient information.

4. The method according to claim 1, wherein:
the processed data comprises a set of joint angular position, a set of speed, a set of acceleration, and a set of torque.

5. The method according to claim 1, wherein:
the set of parameters comprises the range of motion ($\theta_{ROM}$), the peak muscle resistance ($\theta_{ROM}$), the change in peak muscle resistance at the different speeds ($\Delta\tau_{pk}$), the average muscle resistance ($\tau_{avg}$), the catch angle ($\theta_{catch}$) when a catch is present, a max stretch speed before catch ($\omega_{max}$) when the catch is present, and a local max speed during acceleration of the one or more body segments ($\omega_{local,max}$) when the catch is not present.

6. The method according to claim 1, further comprising:
performing a calibration of the PVRM before conducting the test protocol with the PVRM.

7. The method according to claim 1, further comprising:
displaying and recording the set of parameters.

8. The method according to claim 1, wherein:
the spasticity-classification result comprises one of six levels including 0, 1, 2, 3, 4, and 5.

9. The method according to claim 8, wherein:
the rigidity-classifying algorithm comprises a defined Metric of Rigidity (MOR):

$$MOR=(f\times\tau_{avg})+(k\times\tau_{pk}),$$

wherein:
    f and k are constants; and
    f>0 and k>0.

10. The method according to claim 1, wherein:
the rigidity-classification result comprises one of five levels including 0, 1, 2, 3, and 4.

11. The method according to claim 1, wherein:
the PVRM comprises a primary module and a secondary module.

12. The method according to claim 11, wherein:
the primary module comprises an angular and velocity sensor, a battery, and a microcontroller; and
the secondary module comprises an angular and velocity sensor, a load sensing sensor, a cover plate, and a housing.

13. The method according to claim 1, wherein:
the PVRM comprises one or more primary modules and one or more secondary modules; and
the joint comprising at least one of a shoulder, an elbow, a wrist, a hip, a knee, or an ankle.

14. The method according to claim 1, further comprising:
assessing a muscle strength based on a product of a measured load multiplied by a moment arm according to the processed data.

15. An apparatus for measuring and assessing limb movement properties, the apparatus comprising:
a position, velocity, and resistance meter (PVRM) disposed on one or more body segments connected by a joint of a subject; and
an electronic device in communication with the PVRM, the electronic device comprising:
a memory for storing instructions, and
a processor in communication with the memory, when the processor executes the instructions, the processor is configured to cause the apparatus to:
conduct a test protocol with the PVRM, wherein the test protocol comprises passive manipulation of the one or more body segments multiple times at different speeds,
obtain raw data from the PVRM and transmit the raw data from the PVRM to the electronic device,
process the raw data to obtain processed data,
obtain a set of parameters based on the processed data,
obtain a classification result according to a muscle resistance-related classifying algorithm based on the set of parameters, by:
determining whether a sign of high muscle resistance is present based on the set of parameters;
in response to determining that the sign of high muscle resistance is not present, determining a subject is in a healthy condition; and
in response to determining that the sign of high muscle resistance is present:
determining whether a catch is present and/or a difference in resistance at a slow and fast stretch speed of the different speeds is larger than a pre-determined threshold,
in response to determining that the catch is present and/or the difference in resistance at the slow and fast stretch speed is larger than the pre-determined threshold, determining a spasticity-classification result based on a spasticity-classifying algorithm, and
in response to determining that the catch is not present and the difference in resistance at the slow and fast stretch speed is not larger than the pre-determined threshold, determining a rigidity-classification result based on a rigidity-classifying algorithm, assess a limb movement property according to the classification result;
reconstruct a history of the limb movement property for a treatment plan for the subject;
generate a table or graph of the reconstructed history of the limb movement property for the treatment plan, wherein the treatment plan includes details of timing, type, and intensity of the test protocol conducted; and
display the generated table or graph to show progression of muscle conditions under the treatment plan and display the treatment plan;
wherein the spasticity-classifying algorithm comprises a defined Metric of Spasticity (MOS):

$$MOS=(a\times\tau_{pk})+(b\times\Delta\tau_{pk})+(c\times\tau_{avg})+(d\times\theta_{ROM})+(e\times\theta_{catch})$$

wherein:
$\tau_{pk}$ is a peak muscle resistance;
$\Delta\tau_{pk}$ is a change in peak muscle resistance at the different speeds;
$\tau_{avg}$ is an average muscle resistance;
$\theta_{ROM}$ is a range of motion;
$\theta_{catch}$ is a catch angle;
a, b, c, d, and e are constants;
a>0, b>0, c>0, d<0, e<0; and
|a|>|b|>| c|>| d|>|e|.

16. The apparatus according to claim 15, wherein:
the raw data comprises a set of acceleration data, a set of rotation data, and a set of force data;
the processed data comprises a set of joint angular position, a set of speed, a set of acceleration, and a set of torque; and
the set of parameters comprises the range of motion ($\theta_{ROM}$), the peak muscle resistance ($\theta_{ROM}$), the change in peak muscle resistance at the different speeds ($\Delta\tau_{pk}$), the average muscle resistance ($\tau_{avg}$), the catch angle ($\theta_{catch}$) when a catch is present, a max stretch speed before catch ($\omega_{max}$) when the catch is present, and a local max speed during acceleration of the one or more body segments ($\omega_{local,max}$) when the catch is not present.

17. The apparatus according to claim 15, wherein, when the processor executes the instructions, the processor is further configured to cause the apparatus to:
perform a calibration of the PVRM before the processor is configured to cause the apparatus to conduct the test protocol with the PVRM; and
display and record the set of parameters.

18. The apparatus according to claim 15, wherein:
the rigidity-classifying algorithm comprises a defined Metric of Rigidity (MOR) according to $MOR=(f\times\tau_{avg})+(k\times\tau_{pk})$,
wherein:
f and k are constants; and
f>0 and k>0.

19. The apparatus according to claim 15, wherein, when the processor executes the instructions, the processor is further configured to cause the apparatus to:
assess a muscle strength based on a product of a measured load multiplied by a moment arm according to the processed data.

* * * * *